(12) United States Patent
Dunn

(10) Patent No.: US 11,447,571 B2
(45) Date of Patent: Sep. 20, 2022

(54) ANTI-LAMBDA MYELOMA ANTIGEN (LMA) BINDING PROTEINS TO TREAT LMA-EXPRESSING CANCER AND AUTOIMMUNE DISORDERS

(71) Applicant: HaemaLogix Pty Ltd, Eveleigh (AU)

(72) Inventor: Rosanne Dunn, Eveleigh (AU)

(73) Assignee: HAEMALOGIX PTY LTD, Eveleigh (AU)

( * ) Notice: Subject to any disclaimer, the term of this patent is extended or adjusted under 35 U.S.C. 154(b) by 153 days.

(21) Appl. No.: 16/970,991

(22) PCT Filed: Feb. 20, 2019

(86) PCT No.: PCT/AU2019/050137
§ 371 (c)(1),
(2) Date: Aug. 19, 2020

(87) PCT Pub. No.: WO2019/161443
PCT Pub. Date: Aug. 29, 2019

(65) Prior Publication Data
US 2021/0230309 A1    Jul. 29, 2021

(30) Foreign Application Priority Data

Feb. 20, 2018   (AU) ................................ 2018900534

(51) Int. Cl.
*C07K 16/00* (2006.01)
*C07K 16/42* (2006.01)
*A61P 35/00* (2006.01)

(52) U.S. Cl.
CPC .............. *C07K 16/42* (2013.01); *A61P 35/00* (2018.01); *C07K 2317/21* (2013.01); *C07K 2317/33* (2013.01); *C07K 2317/524* (2013.01); *C07K 2317/526* (2013.01); *C07K 2317/565* (2013.01); *C07K 2317/622* (2013.01); *C07K 2317/732* (2013.01); *C07K 2317/734* (2013.01); *C07K 2317/76* (2013.01); *C07K 2317/92* (2013.01)

(58) Field of Classification Search
CPC ........................... C07K 16/42; C07K 2317/21; C07K 2317/33; C07K 2317/565; C07K 2317/622; C07K 2317/732; C07K 2317/734; C07K 2317/76; A61P 35/00
See application file for complete search history.

(56) References Cited

FOREIGN PATENT DOCUMENTS

| WO | 2005/082409 A1 | 9/2005 |
| WO | 2010/088388 A1 | 8/2010 |
| WO | 2010/115238 A1 | 10/2010 |
| WO | 2013/132245 A1 | 9/2013 |

OTHER PUBLICATIONS

Asvadi, P. et al "Identification and Characterisation of Lambda Myeloma Antigen, LMA, as a Therapeutic Target in Lambda Multiple Myeloma" Haematologica, vol. 98, Supp. 1, p. 316, Abstract 756.

*Primary Examiner* — Lei Yao
(74) *Attorney, Agent, or Firm* — Fox Rothschild LLP

(57) ABSTRACT

The present application is directed to anti-lambda myeloma antigen (LMA) binding proteins, wherein the binding protein is an antibody. Compositions comprising these antibodies and nucleic acids encoding these antibodies are also disclosed. These antibodies, compositions and nucleic acids may be used in the treatment of LMA expressing pathologies.

Figure 1:
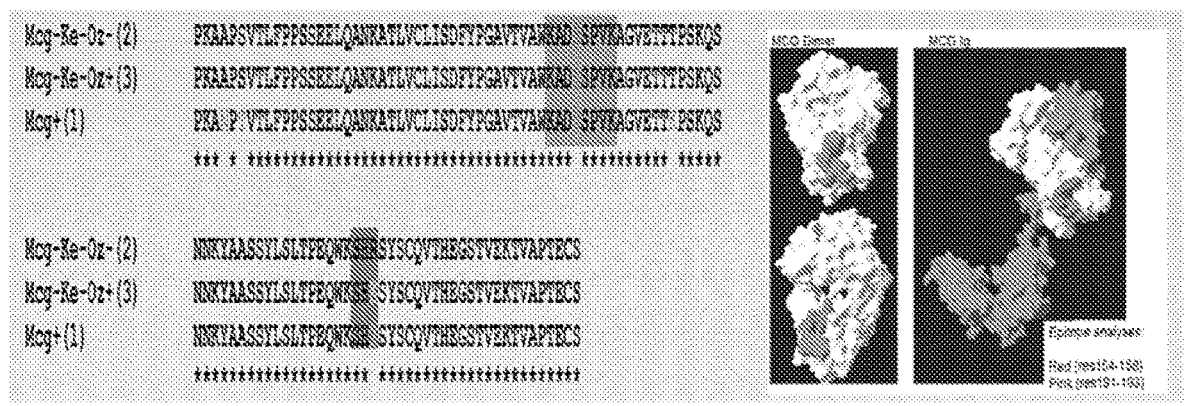

6 Claims, 12 Drawing Sheets
Specification includes a Sequence Listing.

| | |
|---|---|
| 7F11  | MEFGLSWLFLVAILKGVQCEVQLLESGGGLVQPGGSLRLSCAASGFTFSSYAMSWVRQAP |
| 10B3  | MELGLRWVFLVAILEGVQCEVQLVESGGGLVKPGGSLRLSCAASGFTFSSYSMNWVRQAP |
| 18E11 | MELGLRWVFLVAILEGVQCEVQLVESGGGLVKPGGSLRLSCAASGFTFSSYSMNWVRQAP |
| 18E8  | MELGLRWVFLVAILEGVQCEVQLVESGGGLVKPGGSLKLSCAASGFTFSSYSMNWVRQAP |
|       | ** ** * ****** ******* ****** ***** ************ * ****** |
| 7F11  | GKGLEWVSAINNSGGSTYYADSVKGRFTISRDNSKNTLYLQMNSLRAEDTAVYYCAKDQG |
| 10B3  | GKGLEWVSFISSNRNYIYYADSVKGRFTISRDNAKNSLYLQMNSLRAEDTAVYYCASLAN |
| 18E11 | GKGLEWVSFISSNRNYIYYADSVKGRFTISRDNAKNSLYLQMNSLRAEDTAVYYCASLAN |
| 18E8  | GKGLEWVSFISSWSNYIYYADSVKGRFTISRDNAKNSLYLQMNSLRAEDTAVYYCASLAN |
|       | ******* *      *************** ** ****************** |
| 7F11  | WGPLNWFDPWGQGTLVTVSSASTKGPSVFPLAPSSKSTSGGTAALGCLVKDYFPEPVTVS |
| 10B3  | WGT---YFDYWGQGTLVTVSSASTKGPSVFPLAPSSKSTSGGTAALGCLVKDYFPEPVTVS |
| 18E11 | WGT---YFDYWGQGTLVTVSSASTKGPSVFPLAPSSKSTSGGTAALGCLVKDYFPEPVTVS |
| 18E8  | WGT---YFDCWGQGTLVTVSSASTKGPSVFPLAPSSKSTSGGTAALGCLVKDYFPEPVTVS |
|       | **    ** ************************************************ |
| 7F11  | WNSGALTSGVHTFPAVLQSSGLYSLSSVVTVPSSSLGTQTYICNVNHKPSNTKVDKRVEP |
| 10B3  | WNSGALTSGVHTFPAVLQSSGLYSLSSVVTVPSSSLGTQTYICNVNHKPSNTKVDKRVEP |
| 18E11 | WNSGALTSGVHTFPAVLQSSGLYSLSSVVTVPSSSLGTQTYICNVNHKPSNTKVDKRVEP |
| 18E8  | WNSGALTSGVHTFPAVLQSSGLYSLSSVVTVPSSSLGTQTYICNVNHKPSNTKVDKRVEP |
|       | ************************************************************ |
| 7F11  | KSCDKTHTCPPCPAPELLGGPSVFLFPPKPKDTLMISRTPEVTCVVVDVSHEDPEVKFNW |
| 10B3  | KSCDKTHTCPPCPAPELLGGPSVFLFPPKPKDTLMISRTPEVTCVVVDVSHEDPEVKFNW |
| 18E11 | KSCDKTHTCPPCPAPELLGGPSVFLFPPKPKDTLMISRTPEVTCVVVDVSHEDPEVKFNW |
| 18E8  | KSCDKTHTCPPCPAPELLGGPSVFLFPPKPKDTLMISRTPEVTCVVVDVSHEDPEVKFNW |
|       | ************************************************************ |
| 7F11  | YVDGVEVHNAKTKPREEQYNSTYRVVSVLTVLHQDWLNGKEYKCKVSNKALPAPIEKTIS |
| 10B3  | YVDGVEVHNAKTKPREEQYNSTYRVVSVLTVLHQDWLNGKEYKCKVSNKALPAPIEKTIS |
| 18E11 | YVDGVEVHNAKTKPREEQYNSTYRVVSVLTVLHQDWLNGKEYKCKVSNKALPAPIEKTIS |
| 18E8  | YVDGVEVHNAKTKPREEQYNSTYRVVSVLTVLHQDWLNGKEYKCKVSNKALPAPIEKTIS |
|       | ************************************************************ |
| 7F11  | KAKGQPREPQVYTLPPSRDELTKNQVSLTCLVKGFYPSDIAVEWESNGQPENNYKTTPPV |
| 10B3  | KAKGQPREPQVYTLPPSRDELTKNQVSLTCLVKGFYPSDIAVEWESNGQPENNYKTTPPV |
| 18E11 | KAKGQPREPQVYTLPPSRDELTKNQVSLTCLVKGFYPSDIAVEWESNGQPENNYKTTPPV |
| 18E8  | KAKGQPREPQVYTLPPSRDELTKNQVSLTCLVKGFYPSDIAVEWESNGQPENNYKTTPPV |
|       | ************************************************************ |
| 7F11  | LDSDGSFFLYSKLTVDKSRWQQGNVFSCSVMHEALHNHYTQKSLSLSPGK |
| 10B3  | LDSDGSFFLYSKLTVDKSRWQQGNVFSCSVMHEALHNHYTQKSLSLSPGK |
| 18E11 | LDSDGSFFLYSKLTVDKSRWQQGNVFSCSVMHEALHNHYTQKSLSLSPGK |
| 18E8  | LDSDGSFFLYSKLTVDKSRWQQGNVFSCSVMHEALHNHYTQKSLSLSPGK |
|       | ************************************************ |

FIGURE 8

ANTI-LAMBDA MYELOMA ANTIGEN (LMA) BINDING PROTEINS TO TREAT LMA-EXPRESSING CANCER AND AUTOIMMUNE DISORDERS

FIELD OF THE INVENTION

The present disclosure relates to anti-LMA binding proteins. Such binding proteins may be useful for treating disorders associated with aberrant proliferation of plasma cells and/or their precursors.

BACKGROUND OF THE INVENTION

Aberrant proliferation of plasma cells and/or their precursors is a hallmark of various human pathologies. One example is multiple myeloma (MM), a malignancy of bone marrow plasma cells. The disease is characterized by malignant plasma cells which secrete either a lambda or lambda light chain restricted monoclonal paraprotein. Lambda restriction occurs in around 40% of myeloma patients and the expression of lambda myeloma antigen (LMA) is highly restricted to malignant effector cells. Despite recent advances in therapy, multiple myeloma remains incurable. Its clinical course is characterized by an initial response to therapy, followed by repeated relapse with eventual resistance to all forms of treatment. It is also associated with significant morbidity and disability both due to the disease itself and toxicity from available treatments.

Accordingly, new approaches for treating aberrant proliferation of plasma cells and/or their precursors are required.

SUMMARY OF THE INVENTION

When producing the human binding proteins of the present disclosure, the present inventors identified a selection of human antibodies that bind and kill LMA positive cell lines. The present inventors also identified human antibodies with heavy chain modifications that direct preferential binding to LMA (i.e. cell surface antigen) over free lambda light chain (e.g. serum antigen). Such modifications may be incorporated into various binding proteins to preferentially target cells expressing LMA. Such binding proteins may be particularly effective at mediating targeted killing of cells expressing LMA such as LMA-expressing cancer cells.

Accordingly, in a first aspect the present disclosure relates to an anti-lambda myeloma antigen (LMA) binding protein having an antigen binding domain, wherein the antigen binding domain preferentially binds LMA over free lambda light chain and comprises a heavy chain variable region ($V_H$) and a light chain variable region ($V_L$), wherein the $V_H$ comprises a complementarity determining region (CDR) 1 as shown in SEQ ID NO: 1, a CDR2 as shown in SEQ ID NO: 2 and a CDR3 as shown in SEQ ID NO: 3. In another example, the $V_H$ comprises an amino acid sequence shown in SEQ ID NO: 4. In another example, the $V_L$ comprises a CDR1 as shown in SEQ ID NO: 6, a CDR2 as shown in SEQ ID NO: 7 and a CDR3 as shown in SEQ ID NO: 8 or SEQ ID NO: 13. In another example, the $V_L$ comprises an amino acid sequence shown in SEQ ID NO: 9 or SEQ ID NO: 14. In another example, the $V_L$ comprises an amino acid sequence shown in SEQ ID NO: 9. In an example, above referenced binding proteins bind lambda isotypes 2 and 3. In an example, above referenced antibodies do not bind lambda isotype 1. In another example, the above referenced antibodies bind free lambda light chain with a $K_D$ less than $1 \times 10^{10}$ as measured by surface plasmon resonance (SPR). In another example, the above referenced antibodies bind free lambda light chain with a $K_D$ less than $5 \times 10^9$ as measured by SPR. In another example, the above referenced antibodies bind free lambda light chain with a $K_D$ less than $1 \times 10^9$ as measured by SPR. In another example, the above referenced antibodies bind free lambda light chain with a $K_D$ less than $5 \times 10^8$ as measured by SPR. In another example, the above referenced antibodies bind free lambda light chain with a $K_D$ less than $5 \times 10^7$ as measured by SPR.

In another example, the present disclosure encompasses an anti-LMA binding protein having an antigen binding domain, wherein the antigen binding domain binds to LMA and comprises a $V_H$ and a $V_L$, wherein:
the $V_H$ comprises a CDR1 as shown in SEQ ID NO: 31, a CDR2 as shown in SEQ ID NO: 32 and a CDR3 as shown in SEQ ID NO: 33 and the $V_L$ comprises a CDR1 as shown in SEQ ID NO: 36 or SEQ ID NO: 41, a CDR2 as shown in SEQ ID NO: 37 or SEQ ID NO: 42 and a CDR3 as shown in SEQ ID NO: 38 or SEQ ID NO: 43; or,
the $V_H$ comprises a CDR1 as shown in SEQ ID NO: 61, a CDR2 as shown in SEQ ID NO: 62 and a CDR3 as shown in SEQ ID NO: 63 and the $V_L$ comprises a CDR1 as shown in SEQ ID NO: 66 or SEQ ID NO: 71, a CDR2 as shown in SEQ ID NO: 67 or SEQ ID NO: 72 and a CDR3 as shown in SEQ ID NO: 68 or SEQ ID NO: 73. In an example, the $V_H$ comprises an amino acid sequence shown in SEQ ID NO: 34 or SEQ ID NO: 64. In another example, the $V_L$ comprises an amino acid sequence shown in any one of SEQ ID NOs: 39, 44, 69 or 74.

In another example, the present disclosure encompasses an anti-LMA binding protein having an antigen binding domain, wherein the antigen binding domain binds to LMA and comprises a heavy chain variable region ($V_H$) and a light chain variable region ($V_L$), wherein:
the $V_H$ comprises an amino acid sequence shown in SEQ ID NO: 5 and the $V_L$ comprises an amino acid sequence shown in SEQ ID NO: 10 or SEQ ID NO: 15;
the $V_H$ comprises an amino acid sequence shown in SEQ ID NO: 34 and the $V_L$ comprises an amino acid sequence shown in SEQ ID NO: 40 or SEQ ID NO: 45;
the $V_H$ comprises an amino acid sequence shown in SEQ ID NO: 65 and the $V_L$ comprises an amino acid sequence shown in SEQ ID NO: 70 or SEQ ID NO: 75.

In another example, the present disclosure encompasses an anti-LMA binding protein having an antigen binding domain, wherein the antigen binding domain binds to LMA and comprises a heavy chain variable region ($V_H$) and a light chain variable region ($V_L$), wherein:
the $V_H$ comprises CDR1, CDR2 and CDR3 from the amino acid sequence shown in SEQ ID NO: 5 and the $V_L$ comprises CDR1, CDR2 and CDR3 from the amino acid sequence shown in SEQ ID NO: 10 or SEQ ID NO: 15;
the $V_H$ comprises CDR1, CDR2 and CDR3 from the amino acid sequence shown in SEQ ID NO: 34 and the $V_L$ comprises CDR1, CDR2 and CDR3 from the amino acid sequence shown in SEQ ID NO: 40 or SEQ ID NO: 45;
the $V_H$ comprises CDR1, CDR2 and CDR3 from the amino acid sequence shown in SEQ ID NO: 65 and the $V_L$ comprises CDR1, CDR2 and CDR3 from the amino acid sequence shown in SEQ ID NO: 70 or SEQ ID NO: 75;
wherein the CDRs are assigned using Kabat.

In another example, the present disclosure encompasses an anti-LMA binding protein having an antigen binding domain, wherein the antigen binding domain binds to LMA and comprises a heavy chain variable region ($V_H$) and a light chain variable region ($V_L$), wherein:
- the $V_H$ comprises CDR1, CDR2 and CDR3 from the amino acid sequence shown in SEQ ID NO: 5 and the $V_L$ comprises CDR1, CDR2 and CDR3 from the amino acid sequence shown in SEQ ID NO: 10 or SEQ ID NO: 15;
- the $V_H$ comprises CDR1, CDR2 and CDR3 from the amino acid sequence shown in SEQ ID NO: 34 and the $V_L$ comprises CDR1, CDR2 and CDR3 from the amino acid sequence shown in SEQ ID NO: 40 or SEQ ID NO: 45;
- the $V_H$ comprises CDR1, CDR2 and CDR3 from the amino acid sequence shown in SEQ ID NO: 65 and the $V_L$ comprises CDR1, CDR2 and CDR3 from the amino acid sequence shown in SEQ ID NO: 70 or SEQ ID NO: 75;

wherein the CDRs are assigned using IMGT.

In another example, a binding protein disclosed herein specifically binds LMA. In another example, a binding protein disclosed herein is an antibody. In an example, the antibody specifically binds LMA. In an example, the antibody is a human antibody. In an example, the $V_H$ and $V_L$ of a binding protein disclosed herein are in a single polypeptide chain. For example, the binding protein may be:
 (i) a single chain Fv fragment (scFv);
 (ii) a dimeric scFv (di-scFv);
 (iii) a trimeric scFv (tri-scFv);
 (iv) any one of (i), (ii) or (iii) linked to a constant region of an antibody, Fc or a heavy chain constant domain $C_H2$ and/or $C_H3$.

In another example, the $V_H$ and $V_L$ of a binding protein disclosed herein are in a separate polypeptide chain. For example, the binding protein may be:
 (i) a diabody;
 (ii) a triabody;
 (iii) a tetrabody;
 (iv) a Fab;
 (v) a F(ab')$_2$;
 (vi) a Fv;
 (vii) one of (i) to (vi) linked to a constant region of an antibody, Fc or a heavy chain constant domain $C_H2$ and/or $C_H3$; or,
 (viii) an intact antibody.

In another example, the present disclosure encompasses a nucleic acid encoding a binding protein disclosed herein. In another example, the present disclosure encompasses a vector comprising a nucleic acid encoding a binding protein disclosed herein. In an example, such a vector can be provided in a host cell for expression of the nucleic acid. Accordingly, in an example, the present disclosure encompasses an isolated or recombinant cell expressing a binding protein defined herein.

In another example, the present disclosure encompasses a composition comprising a pharmaceutical carrier and either a binding protein defined herein.

In another example, the present disclosure encompasses a method of treating an LMA-expressing cancer in a subject, the method comprising administering to the subject and effective amount of a binding protein defined herein. In another example, the present disclosure encompasses use of a binding protein defined herein in the manufacture of a medicament for treating an LMA-expressing cancer. In another example, the present disclosure encompasses a binding protein defined herein for use in treating an LMA-expressing cancer. In an example, the LMA-expressing cancer is multiple myeloma, Waldenstroms macroglobulinemia, diffuse large B cell lymphoma (DLBCL), POEMS syndrome, or amyloidosis.

In another example, the present disclosure encompasses a method of treating an autoimmune disorder in a subject, the method comprising administering to the subject and effective amount of a binding protein defined herein. In another example, the present disclosure encompasses use of a binding protein defined herein in the manufacture of a medicament for treating an autoimmune disorder. In another example, the present disclosure encompasses a binding protein defined herein for use in treating an autoimmune disorder. In an example, the autoimmune disorder is selected from the group consisting of rheumatoid arthritis, systemic lupus erythematosus, diabetes mellitus, and multiple sclerosis.

Any example herein shall be taken to apply mutatis mutandis to any other example unless specifically stated otherwise.

The present disclosure is not to be limited in scope by the specific examples described herein, which are intended for the purpose of exemplification only. Functionally-equivalent products, compositions and methods are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The disclosure is hereinafter described by way of the following non-limiting Examples and with reference to the accompanying drawings.

BRIEF DESCRIPTION OF THE ACCOMPANYING DRAWINGS

FIG. 1. The 4G7 monoclonal antibody epitope on lambda free light chain. The panel on the left shows the alignment of the amino acid sequence of lambda free light chains 1, 2 and 3 isotypes whereby lambda isotypes 2 and 3 constitutes 95% of the expressed lambda light chain repertoire. Asterisks denote sequence identity. The divergent amino acids are highlighted. The right panel shows identified peptides in 3D structure of a lambda light chain dimer (MCG dimer) and the MCG Ig demonstrating that within the folded light chain protein the two peptides form a contagion to create a non-idiotypic conformational epitope.

Figure 2A:
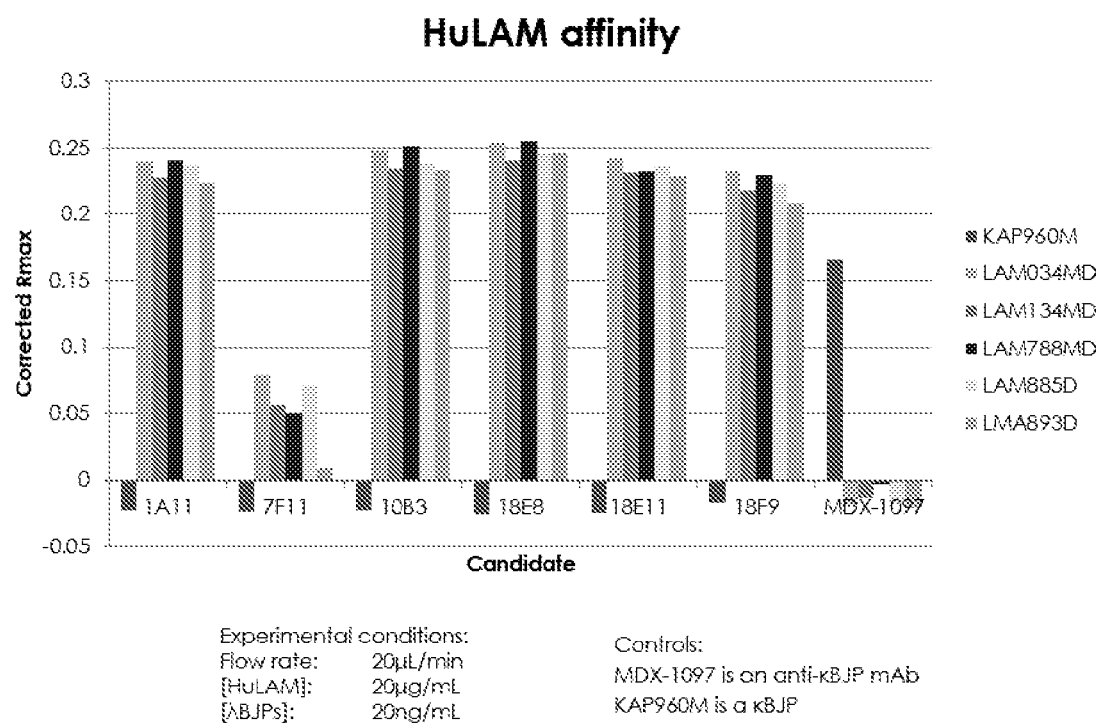

FIG. 2. Affinity of human anti-LMA antibodies to purified lambda-light chains. (A) The graph depicts the SPR values 4G7. of human anti-LMA antibody clones (1A11, 7F11, 10B3, 18E8, 18E11 and 18F9) (20 µg/mL) against purified lambda-light chains BJP (LAM034MD, LAM134MD, MAL788MD, LAM885D, LAM893D) (20 ng/mL). Anti-κBJP monoclonal antibody MDX-1097 and κBJP (20 ng/mL) (KAP960M) were used as negative controls. Human anti-LMA antibody clones, apart from 7F11, demonstrated high and comparable selective affinity to purified lambda-light chains BJP; 7F11 demonstrated lower affinity. Abbreviations at the end of the lambda-light chains BJP: M: monomer; MD: mixture of monomer and dimeric forms; D: dimer. (B) The graph depicts the SPR values of human anti-LMA antibody clones (18E8, 7F11 and 18F9) (700 ng/mL) to commercial lambda-light chain (Bethyl). Human anti-LMA antibody 7F11 weakly binds to commercial lambda-light chain (Bethyl) compared to clones 18E8 and 18F9.

Figure 3:
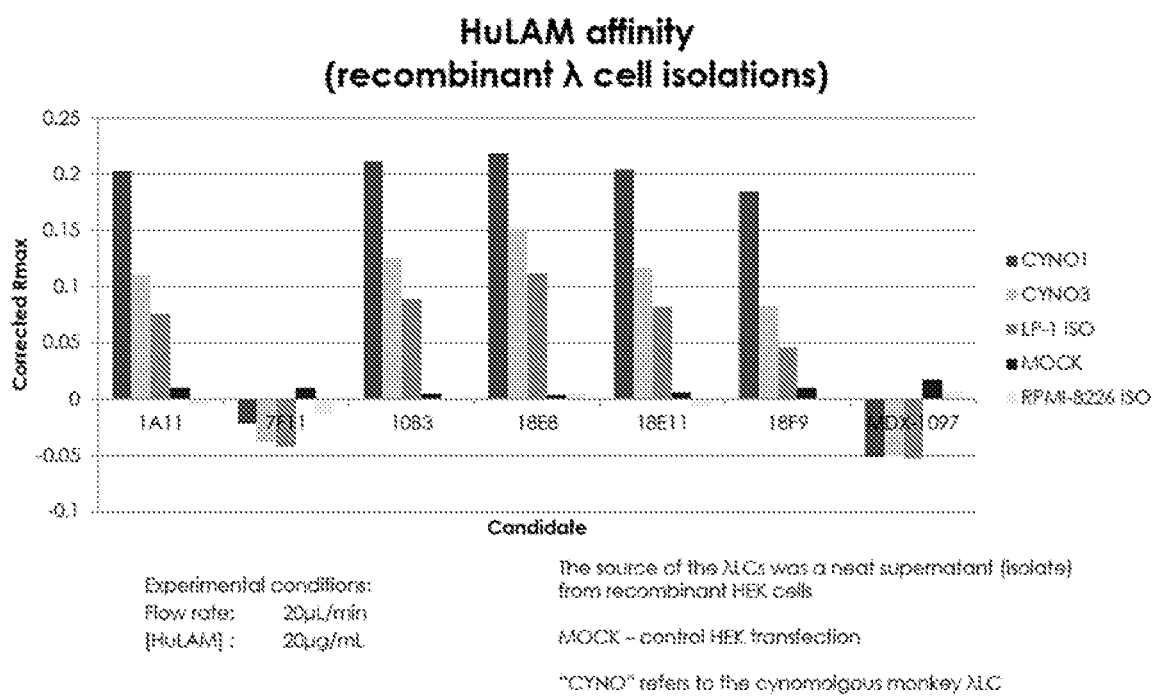

FIG. 3. Affinity of human anti-LMA antibodies to recombinant lambda-light chain isolates from HEK cells. The graph depicts the SPR values of human anti-LMA antibody candidates (1A11, 7F11, 10B3, 18E8, 18E11, 18F9) (20 µg/mL) against cynomologus monkey lambda-light chains (CYNO1, CYNO3), supernatant from lambda-light chain transfected HEK cells, LP-1 lambda-light chain isolate (LP-1 ISO) and RPMI-8226 lambda-light chain isolate (RPMI-8226 ISO). Anti-κBJP monoclonal antibody MDX-1097 was used as a negative control. Human anti-LMA antibody clones, apart from 7F11, demonstrated high and comparable selective affinity to cynomologus monkey lambda-light chains and lambda-light chain isolates from HEK, LP-1 and RPMI-8226; 7F11 demonstrated low affinity.

Figure 4:
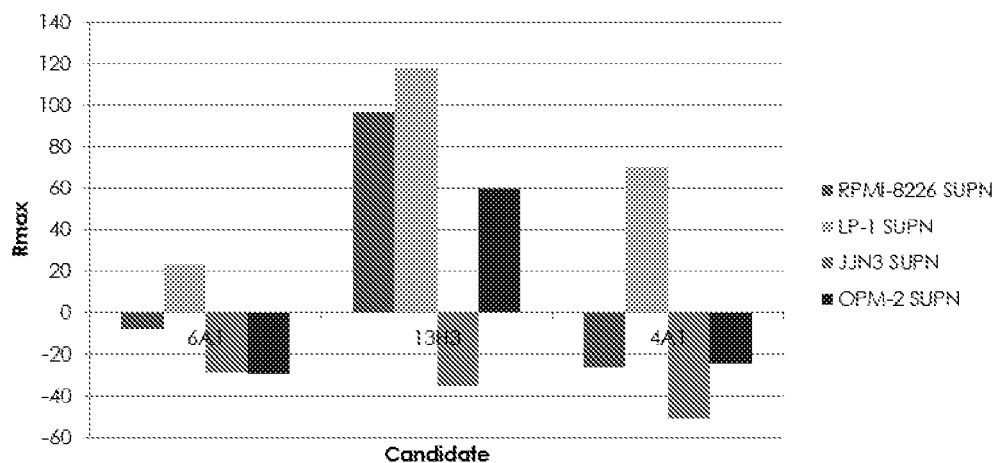

FIG. 4. Affinity of human anti-LMA antibodies to supernatant human multiple myeloma cell lines. The graph depicts the SPR values of human anti-LMA antibody candidates (6A1, 13H3 and 4A1) (20 µg/mL) against supernatant from human multiple myeloma cell lines (RPMI-8226 (lambda isotype 2), LP-1 (lambda isotype 1), JJN3 (kappa), OPM-2 (lambda isotype 3). Human anti-LMA antibody clones demonstrated high and selective affinity to soluble lambda light chain isotypes expressed by human multiple myeloma cell lines and not to kappa-light chain expressed by the JJN3 cell line.

Figure 5A:
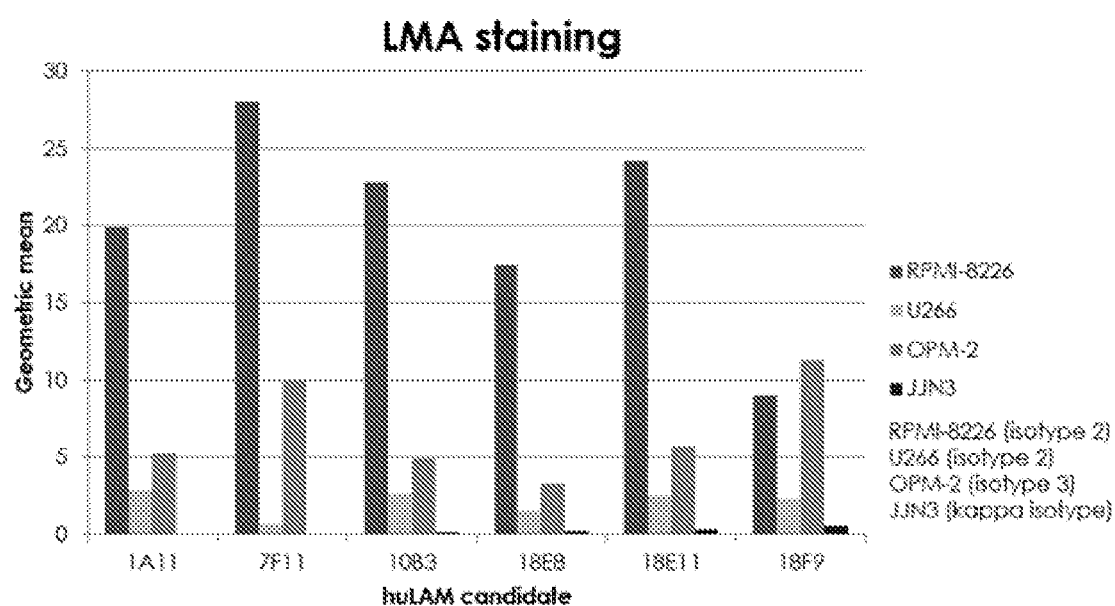

FIG. 5. Binding of human anti-LMA antibodies to LMA positive human myeloma cell lines. (A) The graph depicts the relative staining (geometric mean) of LMA positive human myeloma cell lines (RPMI-8226 (lambda isotype 2), U266 (lambda isotype 2), JJN3 (kappa), OPM-2 (lambda isotype 3)) by the human anti-LMA antibody candidates (1A11, 7F11, 10B3, 18E8, 18E11 and 18F9) compared to no primary antibody control as determined by flow cytometric analysis. Human anti-LMA antibodies demonstrated selective staining of all tested human myeloma cell lines but did not (or weakly) stained JJN3 (kappa) cell line. (B) The graph depicts the relative staining (geometric mean) of LMA positive human myeloma cell lines (U266 (lambda isotype 2), OPM-2 (lambda isotype 3) and KMS-18 (lambda isotype 1) by the human anti-LMA antibody candidates (1A11, 7F11, 10B3, 18E8, 18E11, 18F9, 6A1, 4A1 and 13H3) compared to no primary antibody control as determined by flow cytometric analysis.

Figure 6:
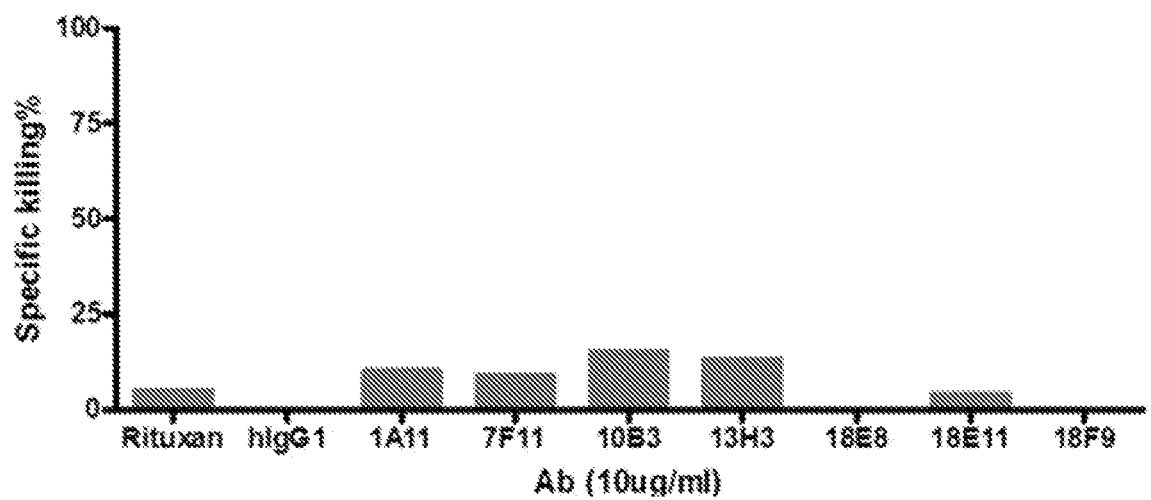

FIG. 6. Antibody dependent cellular cytotoxicity (ADCC) on myeloma cells.

Figure 7:
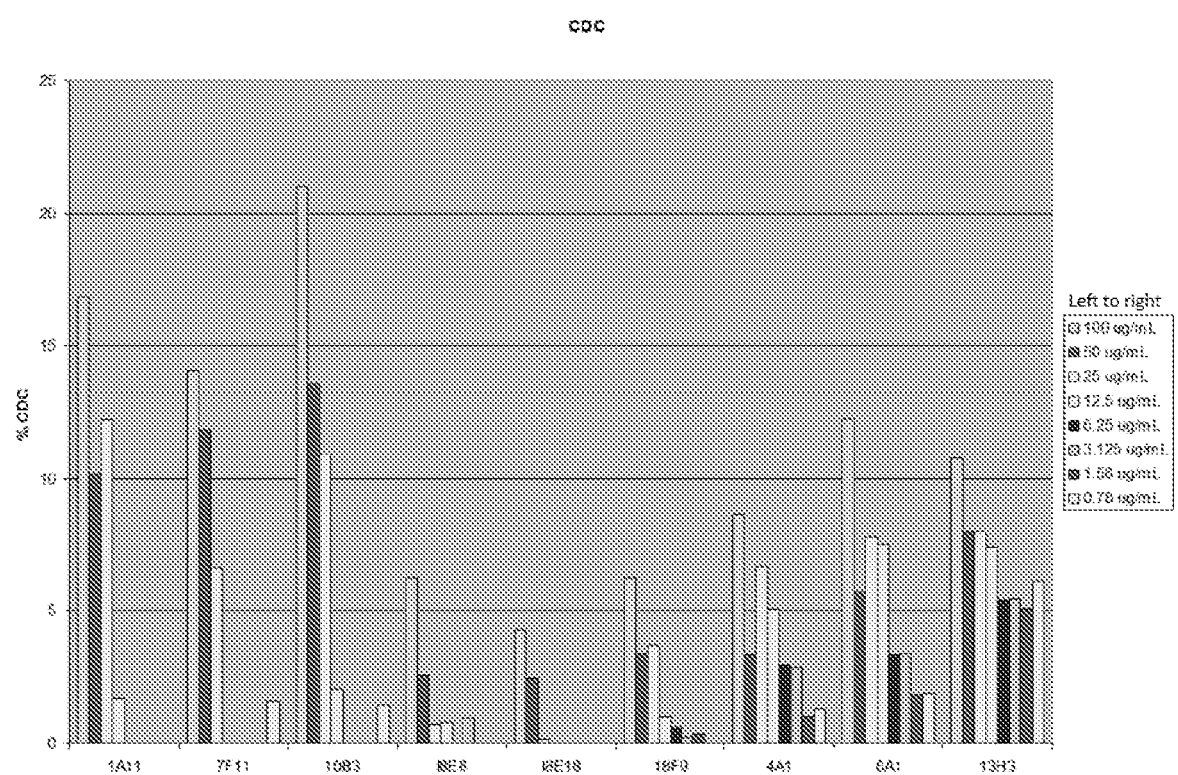

FIG. 7. Complement mediated cytotoxicity (CDC) on myeloma cells.

FIG. 8. Sequence alignment comparing 7F11 with 10B3, 18E11 and 18E8. Heavy chain CDRs underlined. Asterisks denote sequence identity.

Figure 9:
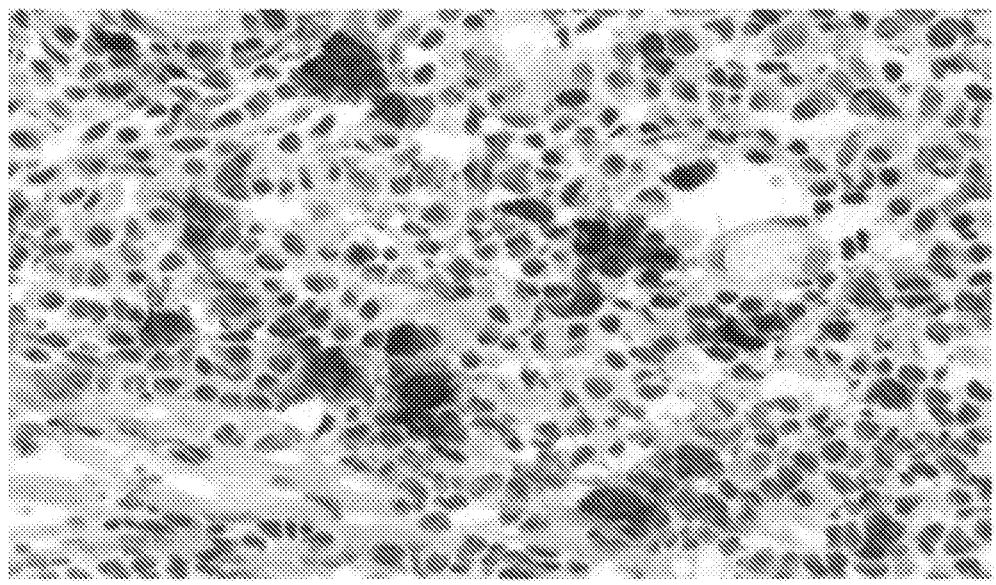
Figure 10:
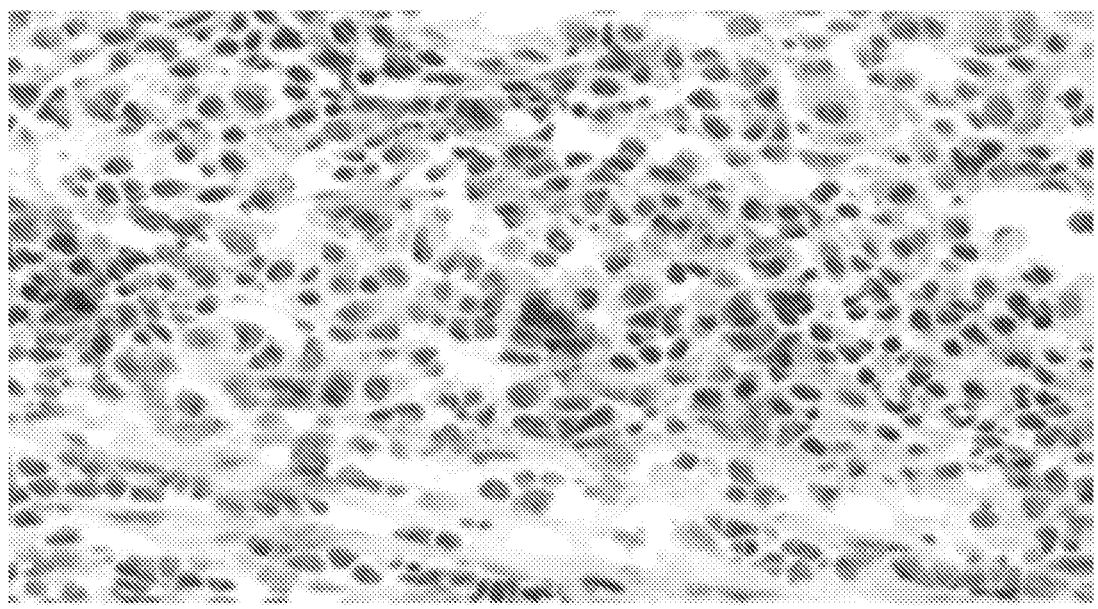

FIG. 9. Cryosection of human tonsil (HT2449-1) stained with 10B3 at 10 µg/mL. 40× objective FIG. 10. Cryosection of human tonsil (HT2449-1) stained with 7F11 at 10 µg/mL. 40× objective.

KEY TO SEQUENCE LISTING

NB: Kabat numbering system used to assign CDRs and Framework sequences
SEQ ID NO: 1—7F11 heavy chain CDR1 amino acid sequence
SEQ ID NO: 2—7F11 heavy chain CDR2 amino acid sequence
SEQ ID NO: 3—7F11 heavy chain CDR3 amino acid sequence
SEQ ID NO: 4—7F11 heavy chain frame work amino acid sequence
SEQ ID NO: 5—7F11 heavy chain full length amino acid sequence
SEQ ID NO: 6—7F11 light chain 1—CDR1 amino acid sequence
SEQ ID NO: 7—7F11 light chain 1—CDR2 amino acid sequence
SEQ ID NO: 8—7F11 light chain 1—CDR3 amino acid sequence
SEQ ID NO: 9—7F11 light chain 1—frame work amino acid sequence
SEQ ID NO: 10—7F11 light chain 1—full length amino acid sequence
SEQ ID NO: 11—7F11 light chain 2—CDR1 amino acid sequence
SEQ ID NO: 12—7F11 light chain 2—CDR2 amino acid sequence
SEQ ID NO: 13—7F11 light chain 2—CDR3 amino acid sequence
SEQ ID NO: 14—7F11 light chain 2—frame work amino acid sequence
SEQ ID NO: 15—7F11 light chain 2—full length amino acid sequence
SEQ ID NO: 16—7F11 heavy chain CDR1 DNA sequence
SEQ ID NO: 17—7F11 heavy chain CDR2 DNA sequence
SEQ ID NO: 18—7F11 heavy chain CDR3 DNA sequence
SEQ ID NO: 19—7F11 heavy chain frame work DNA sequence
SEQ ID NO: 20—7F11 heavy chain full length DNA sequence
SEQ ID NO: 21—7F11 light chain 1—CDR1 DNA sequence
SEQ ID NO: 22—7F11 light chain 1—CDR2 DNA sequence
SEQ ID NO: 23—7F11 light chain 1—CDR3 DNA sequence
SEQ ID NO: 24—7F11 light chain 1—frame work DNA sequence
SEQ ID NO: 25—7F11 light chain 1—full length DNA sequence
SEQ ID NO: 26—7F11 light chain 2—CDR1 DNA sequence
SEQ ID NO: 27—7F11 light chain 2—CDR2 DNA sequence
SEQ ID NO: 28—7F11 light chain 2—CDR3 DNA sequence
SEQ ID NO: 29—7F11 light chain 2—frame work DNA sequence
SEQ ID NO: 30—7F11 light chain 2—full length DNA sequence
SEQ ID NO: 31—18E8 heavy chain CDR1 amino acid sequence
SEQ ID NO: 32—18E8 heavy chain CDR2 amino acid sequence
SEQ ID NO: 33—18E8 heavy chain CDR3 amino acid sequence
SEQ ID NO: 34—18E8 heavy chain frame work amino acid sequence
SEQ ID NO: 35—18E8 heavy chain full length amino acid sequence
SEQ ID NO: 36—18E8 light chain 1—CDR1 amino acid sequence SEQ ID NO: 37—18E8 light chain 1—CDR2 amino acid sequence
SEQ ID NO: 38—18E8 light chain 1—CDR3 amino acid sequence
SEQ ID NO: 39—18E8 light chain 1—frame work amino acid sequence
SEQ ID NO: 40—18E8 light chain 1—full length amino acid sequence
SEQ ID NO: 41—18E8 light chain 2—CDR1 amino acid sequence
SEQ ID NO: 42—18E8 light chain 2—CDR2 amino acid sequence
SEQ ID NO: 43—18E8 light chain 2—CDR3 amino acid sequence
SEQ ID NO: 44—18E8 light chain 2—frame work amino acid sequence
SEQ ID NO: 45—18E8 light chain 2—full length amino acid sequence
SEQ ID NO: 46—18E8 heavy chain CDR1 DNA sequence
SEQ ID NO: 47—18E8 heavy chain CDR2 DNA sequence
SEQ ID NO: 48—18E8 heavy chain CDR3 DNA sequence
SEQ ID NO: 49—18E8 heavy chain frame work DNA sequence
SEQ ID NO: 50—18E8 heavy chain full length DNA sequence
SEQ ID NO: 51—18E8 light chain 1—CDR1 DNA sequence
SEQ ID NO: 52—18E8 light chain 1—CDR2 DNA sequence
SEQ ID NO: 53—18E8 light chain 1—CDR3 DNA sequence
SEQ ID NO: 54—18E8 light chain 1—frame work DNA sequence
SEQ ID NO: 55—18E8 light chain 1—full length DNA sequence
SEQ ID NO: 56—18E8 light chain 2—CDR1 DNA sequence
SEQ ID NO: 57—18E8 light chain 2—CDR2 DNA sequence
SEQ ID NO: 58—18E8 light chain 2—CDR3 DNA sequence
SEQ ID NO: 59—18E8 light chain 2—frame work DNA sequence
SEQ ID NO: 60—18E8 light chain 2—full length DNA sequence
SEQ ID NO: 61—10B3 heavy chain CDR1 amino acid sequence
SEQ ID NO: 62—10B3 heavy chain CDR2 amino acid sequence
SEQ ID NO: 63—10B3 heavy chain CDR3 amino acid sequence
SEQ ID NO: 64—10B3 heavy chain frame work amino acid sequence
SEQ ID NO: 65—10B3 heavy chain full length amino acid sequence
SEQ ID NO: 66—10B3 light chain 1—CDR1 amino acid sequence
SEQ ID NO: 67—10B3 light chain 1—CDR2 amino acid sequence
SEQ ID NO: 68—10B3 light chain 1—CDR3 amino acid sequence
SEQ ID NO: 69—10B3 light chain 1—frame work amino acid sequence
SEQ ID NO: 70—10B3 light chain 1—full length amino acid sequence
SEQ ID NO: 71—10B3 light chain 2—CDR1 amino acid sequence
SEQ ID NO: 72—10B3 light chain 2—CDR2 amino acid sequence
SEQ ID NO: 73—10B3 light chain 2—CDR3 amino acid sequence
SEQ ID NO: 74—10B3 light chain 2—frame work amino acid sequence
SEQ ID NO: 75—10B3 light chain 2—full length amino acid sequence
SEQ ID NO: 76—10B3 heavy chain CDR1 DNA sequence
SEQ ID NO: 77—10B3 heavy chain CDR2 DNA sequence
SEQ ID NO: 78—10B3 heavy chain CDR3 DNA sequence
SEQ ID NO: 79—10B3 heavy chain frame work DNA sequence
SEQ ID NO: 80—10B3 heavy chain full length DNA sequence
SEQ ID NO: 81—10B3 light chain 1—CDR1 DNA sequence
SEQ ID NO: 82—10B3 light chain 1—CDR2 DNA sequence
SEQ ID NO: 83—10B3 light chain 1—CDR3 DNA sequence
SEQ ID NO: 84—10B3 light chain 1—frame work DNA sequence
SEQ ID NO: 85—10B3 light chain 1—full length DNA sequence
SEQ ID NO: 86—10B3 light chain 2—CDR1 DNA sequence
SEQ ID NO: 87—10B3 light chain 2—CDR2 DNA sequence
SEQ ID NO: 88—10B3 light chain 2—CDR3 DNA sequence
SEQ ID NO: 89—10B3 light chain 2—frame work DNA sequence
SEQ ID NO: 90—10B3 light chain 2—full length DNA sequence
SEQ ID NO: 91—4G7 epitope (lambda isotype 2 and 3) epitope 1
SEQ ID NO: 92—4G7 epitope (lambda isotype 2 and 3) epitope 2
SEQ ID NO: 93—4G7 epitope (lambda isotype 1) epitope 1
SEQ ID NO: 94—4G7 epitope (lambda isotype 1) epitope 2

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., molecular biology, biochemistry, antibodies, antibody fragments and clinical studies).

"Lambda myeloma antigen" (LMA) is a cell membrane antigen that is found on the surface of plasma cells such as malignant myeloma cells and, in some cases, non-malignant plasma cell precursors such as plasmablasts. Specifically, LMA consists of free lambda light chains expressed on the cell membrane. Anti-LMA binding proteins encompassed by the present disclosure specifically recognize a conformational epitope on the lambda light chain that is only available for binding when the lambda light chain is not associated with a heavy chain. Accordingly, anti-LMA binding proteins encompassed by the present disclosure do not bind to intact lambda-chain containing IgG, IgM, IgE or IgA.

As used herein, the term "binds" in reference to the interaction of a binding protein described herein and LMA means that the interaction is dependent upon the presence of a particular structure (e.g., an antigenic determinant or epitope) on LMA. For example, a binding protein recognizes and binds to a specific antigen structure rather than to antigens generally. For example, if a binding protein binds to epitope "A", the presence of a molecule containing epitope "A" (or free, unlabelled "A"), in a reaction containing labelled "A" and the binding protein, will reduce the amount of labelled "A" bound to the binding protein. In an example, an LMA binding protein disclosed herein preferentially binds LMA (i.e. cell surface antigen) over free lambda light chain (e.g. serum antigen). A binding protein disclosed herein that preferentially binds LMA over free lambda light chain reacts or associates more frequently, more rapidly, with greater duration and/or with greater affinity with LMA than it does with free light chain.

As used herein, the term "specifically binds" shall be taken to mean that the binding interaction between a binding protein and LMA is dependent on detection of the LMA by the binding protein. Accordingly, the binding protein specifically binds or recognizes LMA even when present in a mixture of other molecules, cells or organisms. In one example, the binding protein reacts or associates more frequently, more rapidly, with greater duration and/or with greater affinity with LMA than it does with alternative antigens or cells. In an example, a binding protein disclosed herein that specifically binds LMA can also preferentially bind or recognize LMA over free light chain. It is also understood by reading this definition that, for example, a binding protein that specifically binds to LMA may or may not specifically bind to a second antigen. As such, "specific binding" does not necessarily require exclusive binding or non-detectable binding of another antigen. The term "specifically binds" can be used interchangeably with "selectively binds" herein. Generally, reference herein to binding means specific binding, and each term shall be understood to provide explicit support for the other term. Methods for determining specific binding will be apparent to the skilled person. For example, a binding protein of the disclosure is contacted with LMA or an alternative antigen. Binding of the binding protein to LMA or alternative antigen is then determined and a binding protein that binds as set out above to the LMA rather than the alternative antigen is considered to specifically bind to LMA. A similar method may be used to identify preferential binding. In this instance, the alternative antigen would be free light chain.

The term "immunoglobulin" will be understood to include an anti-LMA binding protein comprising an immunoglobulin domain. Exemplary immunoglobulins are antibodies. Additional proteins encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. Other "immunoglobulins" include T cell receptors.

The term "binding protein" is used in the context of the present disclosure to refer to human immunoglobulin molecules immunologically reactive with a particular antigen and includes both polyclonal and monoclonal antibodies. The term "binding protein" also includes antigen binding forms of antibodies, including fragments with antigen-binding capability (e.g., Fab', F(ab')$_2$, Fab, Fv and rIgG as discussed in Pierce Catalogue and Handbook, 1994-1995 (Pierce Chemical Co., Rockford, Ill.); Kuby, J., Immunology, 3$^{rd}$ Ed., W.H. Freeman & Co., New York (1998). The term is also used to refer to recombinant single chain Fv fragments (scFv) as well as divalent (di-scFv) and trivalent (tri-scFV) forms thereof. The term antibody also includes diabodies, triabodies, and tetrabodies.

An "antigen binding fragment" of an antibody comprises one or more variable regions of an intact antibody. Examples of antibody fragments include Fab, Fab', F(ab')2 and Fv fragments; diabodies; linear antibodies and single-chain antibody molecules formed from antibody fragments. For example, the term antigen binding fragment may be used to refer to recombinant single chain Fv fragments (scFv) as well as divalent (di-scFv) and trivalent (tri-scFV) forms thereof.

Such fragments can be produced via various methods known in the art.

The terms "full-length antibody", "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

The term "complementarity determining region" or "CDR" is used in the context of the present disclosure to refer to the part of the two variable chains of antibodies (heavy and light chains) that recognize and bind to the particular antigen. The CDRs are the most variable portion of the variable chains and provide binding proteins with their specificity. There are generally three CDRs on each of the variable heavy ($V_H$) and variable light ($V_L$) chains.

As used herein, "variable region" refers to the portions of the light and/or heavy chains of an antibody as defined herein that specifically binds to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system" or "Kabat".

Other conventions that include corrections or alternate numbering systems for variable domains include IMGT (Lefranc, et al. (2003), Dev Comp Immunol 27: 55-77), Chothia (Chothia C, Lesk A M (1987), J Mal Biol 196: 901-917; Chothia, et al. (1989), Nature 342: 877-883) and AHo (Honegger A, Plückthun A (2001) J Mol Biol 309: 657-670). For convenience, examples of binding proteins of the present disclosure may also be labelled according to IMGT.

The term "constant region" as used herein, refers to a portion of heavy chain or light chain of an antibody other than the variable region. In a heavy chain, the constant region generally comprises a plurality of constant domains and a hinge region, e.g., a IgG constant region comprises the following linked components, a constant heavy $C_H1$, a linker, a $C_H2$ and a $C_H3$. In a heavy chain, a constant region comprises a Fc. In a light chain, a constant region generally comprises one constant domain (a CL1).

The term "fragment crystalizable" or "Fc" or "Fc region" or "Fc portion" (which can be used interchangeably herein) refers to a region of an antibody comprising at least one constant domain and which is generally (though not necessarily) glycosylated and which is capable of binding to one or more Fc receptors and/or components of the complement cascade. The heavy chain constant region can be selected from any of the five isotypes: α, δ, ε, γ, or μ. Exemplary heavy chain constant regions are gamma 1 (IgG1), gamma 2 (IgG2) and gamma 3 (IgG3), or hybrids thereof.

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α or δ heavy chain comprises two constant domains.

The term "antibody heavy chain" is used herein to refer to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. κ and λ light chains refer to the two major antibody light chain isotypes.

The term "naked" is used to refer to binding proteins of the present disclosure that are not conjugated to another compound, e.g., a toxic compound or radiolabel. For example, the term "naked" can be used to refer to binding proteins that are not conjugated to another compound. Accordingly, in one example, the binding proteins of the present disclosure are "naked". Put another way, the binding proteins of the present disclosure can be un-conjugated.

In contrast, the term "conjugated" is used in the context of the present disclosure to refer to binding proteins described herein that are conjugated to another compound, e.g., a toxic compound such as a cytotoxic agent or radiolabel. Accordingly, in one example, a binding protein of the present disclosure is "conjugated".

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, Bi, P, Pb and radioactive isotopes of Lu), chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

Terms such as "host cell," "host cell line," and "host cell culture" are used interchangeably in the context of the present disclosure to refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "isolated nucleic acid" according to the present disclosure is a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "expression vector" as used herein refers to a vector comprising a recombinant nucleic acid sequence comprising at least one expression control sequence operatively linked to the nucleic acid sequence to be expressed. An expression vector comprises all necessary cis acting elements required for expression. Examples of expression vectors include, but are not limited to, plasmids, cosmids, and viruses that encode the recombinant polynucleotide to be expressed. In other examples, the expression vector comprises transposable elements that are capable of integrating into the genome, for example, the PiggyBac expression system. In another example, the expression vector is a viral vector that allows for integration of the expression vector contents into the host genome, for example retroviral and lentiviral vectors.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill of those practicing in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

Binding proteins according to the present disclosure and compositions comprising the same can be administered to a subject to treat various indications. Terms such as "subject", "patient" or "individual" are terms that can, in context, be used interchangeably in the present disclosure. In an example, the subject is a mammal. The mammal may be a companion animal such as a dog or cat, or a livestock animal such as a horse or cow. In one example, the subject is a human. For example, the subject can be an adult. In another example, the subject can be a child. In another example, the subject can be an adolescent.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated.

As used herein, the term "prevention" includes providing prophylaxis with respect to occurrence or recurrence of a disease in an individual. An individual may be predisposed to or at risk of developing the disease or disease relapse but has not yet been diagnosed with the disease or the relapse.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is meant an amount necessary to effect treatment of a disease or condition described below. The effective amount may vary according to the disease or condition to be treated and also according to the weight, age, racial background, sex, health and/or physical condition and other factors relevant to the subject being treated. Typically, the effective amount will fall within a relatively broad range (e.g. a "dosage" range) that can be determined through routine trial and experimentation by a medical practitioner.

A "therapeutically effective amount" is at least the minimum concentration required to effect a measurable improvement of a particular disorder (e.g. cancer). A therapeutically effective amount herein may vary according to factors such as the disease state, age, sex, and weight of the patient, and the ability of the binding protein to elicit a desired response in the individual. A therapeutically effective amount is also one in which any toxic or detrimental effects of the binding protein are outweighed by the therapeutically beneficial effects. In the case of cancer, a therapeutically effective amount of a binding protein may reduce the number of cancer cells; reduce the primary tumour size; inhibit (i.e., slow to some extent and, in some examples, stop) cancer cell infiltration into peripheral organs; inhibit (i.e., slow to some extent and, in some examples, stop) tumour metastasis; inhibit or delay, to some extent, tumour growth and tumour progression; and/or relieve to some extent one or more of the symptoms associated with the cancer. To the extent the binding protein may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

Human Binding Proteins

The present disclosure relates to "human" binding proteins. In an example, "human" binding proteins of the present disclosure can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human binding proteins" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. In an example, the term encompasses human antibodies.

Monoclonal antibodies are another exemplary form of binding protein contemplated by the present disclosure. The term "monoclonal antibody" or "MAb" refers to a homogeneous antibody population capable of binding to the same antigen(s), for example, to the same epitope within the antigen. This term is not intended to be limited as regards to the source of the antibody or the manner in which it is made.

The present disclosure also contemplates a deimmunized antibody or antigen binding fragment thereof, e.g., as described in WO2000/34317 and WO2004/108158. Deimmunized antibodies and fragments have one or more epitopes, e.g., B cell epitopes or T cell epitopes removed (i.e., mutated) to thereby reduce the likelihood that a subject will raise an immune response against the antibody or protein. For example, an antibody of the disclosure is analyzed to identify one or more B or T cell epitopes and one or more amino acid residues within the epitope is mutated to thereby reduce the immunogenicity of the antibody.

Antibody Fragments

Single-Domain Antibodies

In some examples, a binding protein of the disclosure is or comprises a single-domain antibody (which is used interchangeably with the term "domain antibody" or "dAb"). A single-domain antibody is a single polypeptide chain comprising all or a portion of the heavy chain variable domain of an antibody.

Single Chain Fv (scFv) Fragments

One of skill in the art will be aware that scFv's comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). Single-chain variable fragments lack the constant Fc region found in complete antibody molecules and therefore can have reduced immunogenicity. Exemplary linkers comprise in excess of 12 amino acid residues with $(Gly_4Ser)_3$ being one of the more favoured linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

In another example, the present disclosure encompasses a dimeric scFv (di-scFV), i.e., a protein comprising two scFv molecules linked by a non-covalent or covalent linkage, e.g., by a leucine zipper domain (e.g., derived from Fos or Jun) or trimeric scFV (tri-scFv). In another example, two scFv's are linked by a peptide linker of sufficient length to permit both scFv's to form and to bind to an antigen, e.g., as described in U.S. Published Application No. 20060263367.

Diabodies, Triabodies, Tetrabodies

In some examples, an antigen binding fragment of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens.

Immunoglobulins and Immunoglobulin Fragments

An example of a binding protein of the present disclosure is a protein (e.g., an antibody mimetic) comprising a variable region of an immunoglobulin, such as a T cell receptor or a heavy chain immunoglobulin (e.g., an IgNAR, a camelid antibody).

V-Like Proteins

An example of a binding protein of the disclosure is a T-cell receptor. T cell receptors have two V-domains that combine into a structure similar to the Fv module of an antibody. Novotny et al., Proc Natl Acad Sci USA 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Affibodies

In a further example, a binding protein of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a binding protein of the disclosure is an Avimer. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see WO2002/088171.

Other Binding Proteins

Other examples of binding proteins encompassed by the present disclosure include:
(i) pepide display scaffolds such as affimers and adhirons (WO2009136182; Tiede et al. (2014) Protein Eng Des Sel 27, 145-155); and,
(ii) centyrins (Jacobs et al. (2012) Protein Eng Des Sel. 25, 107-117; Diem et al. (2014) Protein Eng Des sel. 27, 49-429).

Lambda Myeloma Antigen (LMA) Binding Proteins

Binding proteins defined herein have an antigen binding domain that binds to or specifically binds to Lambda Myeloma Antigen (LMA). In an example, binding proteins defined herein have an antigen binding domain that preferentially binds LMA over free light chain. In one example, anti-LMA binding proteins according to the present disclosure comprise a heavy chain variable region ($V_H$) having a CDR 1 as shown in SEQ ID NO: 1, a CDR2 as shown in SEQ ID NO: 2 and a CDR3 as shown in SEQ ID NO: 3. In another example, the anti-LMA binding proteins comprise a light chain variable region ($V_L$) having a CDR1 as shown in SEQ ID NO: 6, a CDR2 as shown in SEQ ID NO: 7 and a CDR3 as shown in SEQ ID NO: 8 or SEQ ID NO: 13. In another example, the anti-LMA binding proteins comprise a light chain variable region ($V_L$) having a CDR1 as shown in SEQ ID NO: 6, a CDR2 as shown in SEQ ID NO: 7 and a CDR3 as shown in SEQ ID NO: 8. In another example, the anti-LMA binding proteins comprise a light chain variable region ($V_L$) having a CDR1 as shown in SEQ ID NO: 6, a CDR2 as shown in SEQ ID NO: 7 and a CDR3 as shown in SEQ ID NO: 13. Accordingly, in another example, the anti-LMA binding proteins comprise a $V_H$ having a CDR 1 as shown in SEQ ID NO: 1, a CDR2 as shown in SEQ ID NO: 2 and a CDR3 as shown in SEQ ID NO: 3 and a $V_L$ having a CDR1 as shown in SEQ ID NO: 6, a CDR2 as shown in SEQ ID NO: 7 and a CDR3 as shown in SEQ ID NO: 8. In another example, the anti-LMA binding proteins comprise a $V_H$ having a CDR 1 as shown in SEQ ID NO: 1, a CDR2 as shown in SEQ ID NO: 2 and a CDR3 as shown in SEQ ID NO: 3 and a $V_L$ having a CDR1 as shown in SEQ ID NO: 6, a CDR2 as shown in SEQ ID NO: 7 and a CDR3 as shown in SEQ ID NO: 13. In an embodiment of these examples, the LMA binding protein binds LMA isotype 2 and isotype 3.

In another example, the anti-LMA binding proteins comprise a $V_H$ comprising an amino acid sequence at least 95% identical to the sequence shown in SEQ ID NO: 4. In another example, the anti-LMA binding protein comprises a $V_L$ comprising an amino acid sequence at least 95% identical to the sequence shown in SEQ ID NO: 9 or SEQ ID NO: 14. For example, the $V_L$ can comprise an amino acid sequence at least 95% identical to the sequence shown in SEQ ID NO: 9. In another example, the $V_L$ can comprise an amino acid sequence at least 95% identical to the sequence shown in SEQ ID NO: 14. In another example, the $V_H$ comprises an amino acid sequence at least 95% identical to the sequence shown in SEQ ID NO: 5. In another example, the $V_L$ comprises an amino acid sequence at least 95% identical to the sequence shown in SEQ ID NO: 10 or SEQ ID NO: 15. For example, the $V_L$ can comprise an amino acid sequence at least 95% identical to the sequence shown in SEQ ID NO: 10. In another example, the $V_L$ comprises an amino acid sequence at least 95% identical to the sequence shown in SEQ ID NO: 15. Accordingly, in another example, the anti-LMA binding protein comprises a $V_H$ comprising an amino acid sequence at least 95% identical to the sequence shown in SEQ ID NO: 4 and a $V_L$ comprising an amino acid sequence at least 95% identical to the sequence shown in SEQ ID NO: 10 or SEQ ID NO: 15. For example, the $V_H$ can comprise an amino acid sequence at least 95% identical to the sequence shown in SEQ ID NO: 4 and a $V_L$ comprising an amino acid sequence at least 95% identical to the sequence shown in SEQ ID NO: 10. For example, the $V_H$ can comprise an amino acid sequence at least 95% identical to the sequence shown in SEQ ID NO: 4 and a $V_L$ comprising an amino acid sequence shown in SEQ ID NO: 15. In these examples, the $V_H$ and/or $V_L$ can be at least 96%, at least 97%, at least 98% or at least 99% identical to the recited SEQ ID NO.

In another example, the anti-LMA binding proteins comprise a $V_H$ comprising an amino acid sequence shown in SEQ ID NO: 4. In another example, the anti-LMA binding protein comprises a $V_L$ comprising an amino acid sequence shown in SEQ ID NO: 9 or SEQ ID NO: 14. For example, the $V_L$ can comprise an amino acid sequence shown in SEQ ID NO: 9. In another example, the $V_L$ can comprise an amino acid sequence shown in SEQ ID NO: 14. In another example, the $V_H$ comprises an amino acid sequence shown in SEQ ID NO: 5. In another example, the $V_L$ comprises an amino acid sequence shown in SEQ ID NO: 10 or SEQ ID NO: 15. For example, the $V_L$ can comprise an amino acid sequence shown in SEQ ID NO: 10. In another example, the $V_L$ comprises an amino acid sequence shown in SEQ ID NO: 15. Accordingly, in another example, the anti-LMA binding protein comprises a $V_H$ comprising an amino acid sequence shown in SEQ ID NO: 4 and a $V_L$ comprising an amino acid sequence shown in SEQ ID NO: 10 or SEQ ID NO: 15. For example, the $V_H$ can comprise an amino acid sequence shown in SEQ ID NO: 4 and a $V_L$ comprising an amino acid sequence shown in SEQ ID NO: 10. For example, the $V_H$ can comprise an amino acid sequence shown in SEQ ID NO: 4 and a $V_L$ comprising an amino acid sequence shown in SEQ ID NO: 15. In these examples, the binding protein specifically binds LMA. For example, the binding protein can preferentially binds LMA over free lambda light chain.

In another example, the anti-LMA binding proteins comprise a heavy chain variable region ($V_H$) having a CDR1 as shown in SEQ ID NO: 31, a CDR2 as shown in SEQ ID NO:

32 and a CDR3 as shown in SEQ ID NO: 33. In another example, the anti-LMA binding proteins comprise a heavy chain variable region (V$_H$) having a CDR1 as shown in SEQ ID NO: 61, a CDR2 as shown in SEQ ID NO: 62 and a CDR3 as shown in SEQ ID NO: 63. In another example, the anti-LMA binding proteins comprise a light chain variable region (V$_L$) having a CDR1 as shown in SEQ ID NO: 36 or SEQ ID NO: 41, a CDR2 as shown in SEQ ID NO: 37 or SEQ ID NO: 42 and a CDR3 as shown in SEQ ID NO: 38 or SEQ ID NO: 43. For example, the anti-LMA binding protein can comprise a V$_L$ having a CDR1 as shown in SEQ ID NO: 36, a CDR2 as shown in SEQ ID NO: 37 and a CDR3 as shown in SEQ ID NO: 38. In another example, the anti-LMA binding protein can comprise a V$_L$ having a CDR1 as shown in SEQ ID NO: 41, a CDR2 as shown in SEQ ID NO: 42 and a CDR3 as shown in SEQ ID NO: 43. Accordingly, in an example, the anti-LMA binding protein can comprise a heavy chain variable region (V$_H$) having a CDR1 as shown in SEQ ID NO: 31, a CDR2 as shown in SEQ ID NO: 32 and a CDR3 as shown in SEQ ID NO: 33 and a V$_L$ comprising a CDR1 as shown in SEQ ID NO: 36 or SEQ ID NO: 41, a CDR2 as shown in SEQ ID NO: 37 or SEQ ID NO: 42 and a CDR3 as shown in SEQ ID NO: 38 or SEQ ID NO: 43. For example, the anti-LMA binding protein can comprise a heavy chain variable region (V$_H$) having a CDR1 as shown in SEQ ID NO: 31, a CDR2 as shown in SEQ ID NO: 32 and a CDR3 as shown in SEQ ID NO: 33 and a V$_L$ comprising a CDR1 as shown in SEQ ID NO: 36, a CDR2 as shown in SEQ ID NO: 37 and a CDR3 as shown in SEQ ID NO: 38. In another example, the anti-LMA binding protein can comprise a heavy chain variable region (V$_H$) having a CDR1 as shown in SEQ ID NO: 31, a CDR2 as shown in SEQ ID NO: 32 and a CDR3 as shown in SEQ ID NO: 33 and a V$_L$ comprising a CDR1 as shown in SEQ ID NO: 41, a CDR2 as shown in SEQ ID NO: 42 and a CDR3 as shown in SEQ ID NO: 43.

In another example, the anti-LMA binding protein can comprise a heavy chain variable region (V$_H$) having a CDR1 as shown in SEQ ID NO: 61, a CDR2 as shown in SEQ ID NO: 62 and a CDR3 as shown in SEQ ID NO: 63 and a V$_L$ comprising a CDR1 as shown in SEQ ID NO: 66 or SEQ ID NO: 71, a CDR2 as shown in SEQ ID NO: 67 or SEQ ID NO: 72 and a CDR3 as shown in SEQ ID NO: 68 or SEQ ID NO: 73. For example, the anti-LMA binding protein can comprise a heavy chain variable region (V$_H$) having a CDR1 as shown in SEQ ID NO: 61, a CDR2 as shown in SEQ ID NO: 62 and a CDR3 as shown in SEQ ID NO: 63 and a V$_L$ comprising a CDR1 as shown in SEQ ID NO: 66, a CDR2 as shown in SEQ ID NO: 67 and a CDR3 as shown in SEQ ID NO: 68. In another example, the anti-LMA binding protein can comprise a heavy chain variable region (V$_H$) having a CDR1 as shown in SEQ ID NO: 61, a CDR2 as shown in SEQ ID NO: 62 and a CDR3 as shown in SEQ ID NO: 63 and a V$_L$ comprising a CDR1 as shown in SEQ ID NO: 71, a CDR2 as shown in SEQ ID NO: 72 and a CDR3 as shown in SEQ ID NO: 73. In an embodiment of these examples, the LMA binding protein binds LMA isotype 1, 2 and isotype 3.

In another example, the V$_H$ comprises an amino acid sequence at least 95% identical to the sequence shown in SEQ ID NO: 34 or SEQ ID NO: 64. For example, the V$_H$ can comprise an amino acid sequence at least 95% identical to the sequence shown in SEQ ID NO: 34. In another example, the V$_H$ can comprise an amino acid sequence at least 95% identical to the sequence shown in SEQ ID NO: 64. In another example, the V$_L$ comprises an amino acid sequence at least 95% identical to an amino acid sequence shown in any one of SEQ ID NOs: 39, 44, 69 or 74. In another example, V$_H$ comprises an amino acid sequence at least 95% identical to the sequence shown in SEQ ID NO: 34 or SEQ ID NO: 64 and the V$_L$ comprises an amino acid sequence at least 95% identical to an amino acid sequence shown in any one of SEQ ID NOs: 39, 44, 69 of 74. For example, the V$_H$ can comprise an amino acid sequence at least 95% identical to the sequence shown in SEQ ID NO: 34 and the V$_L$ can comprise an amino acid sequence at least 95% identical to the sequence shown in SEQ ID NO: 39. In another example, the V$_H$ can comprise an amino acid sequence at least 95% identical to the sequence shown in SEQ ID NO: 34 and the V$_L$ can comprise an amino acid sequence at least 95% identical to the sequence shown in SEQ ID NO: 44. In another example, the V$_H$ can comprise an amino acid sequence at least 95% identical to the sequence shown in SEQ ID NO: 64 and the V$_L$ can comprise an amino acid sequence at least 95% identical to the sequence shown in SEQ ID NO: 39. In another example, the V$_H$ can comprise an amino acid sequence at least 95% identical to the sequence shown in SEQ ID NO: 64 and the V$_L$ can comprise an amino acid sequence at least 95% identical to the sequence shown in SEQ ID NO: 44. In another example, the V$_H$ can comprise an amino acid sequence at least 95% identical to the sequence shown in SEQ ID NO: 64 and the V$_L$ can comprise an amino acid sequence at least 95% identical to the sequence shown in SEQ ID NO: 69. In another example, the V$_H$ can comprise an amino acid sequence at least 95% identical to the sequence shown in SEQ ID NO: 64 and the V$_L$ can comprise an amino acid sequence at least 95% identical to the sequence shown in SEQ ID NO: 74. In another example, the V$_H$ can comprise an amino acid sequence at least 95% identical to the sequence shown in SEQ ID NO: 5 and the V$_L$ can comprise an amino acid sequence at least 95% identical to the sequence shown in SEQ ID NO: 10 or SEQ ID NO: 15. In another example, the V$_H$ can comprise an amino acid sequence at least 95% identical to the sequence shown in SEQ ID NO: 5 and the V$_L$ can comprise an amino acid sequence at least 95% identical to the sequence shown in SEQ ID NO: 10. In another example, the V$_H$ can comprise an amino acid sequence at least 95% identical to the sequence shown in SEQ ID NO: 5 and the V$_L$ can comprise an amino acid sequence at least 95% identical to the sequence shown in or SEQ ID NO: 15. In another example, the V$_H$ can comprise an amino acid sequence at least 95% identical to the sequence shown in SEQ ID NO: 34 and the V$_L$ can comprise an amino acid sequence at least 95% identical to the sequence shown in SEQ ID NO: 40 or SEQ ID NO: 45. In another example, the V$_H$ can comprise an amino acid sequence at least 95% identical to the sequence shown in SEQ ID NO: 34 and the V$_L$ can comprise an amino acid sequence at least 95% identical to the sequence shown in or SEQ ID NO: 40. In another example, the V$_H$ can comprise an amino acid sequence at least 95% identical to the sequence shown in SEQ ID NO: 34 and the V$_L$ can comprise an amino acid sequence at least 95% identical to the sequence shown in SEQ ID NO: 10 or SEQ ID NO: 45. In another example, the V$_H$ can comprise an amino acid sequence at least 95% identical to the sequence shown in SEQ ID NO: 65 and the V$_L$ can comprise an amino acid sequence at least 95% identical to the sequence shown in SEQ ID NO: 70 or SEQ ID NO: 75. In another example, the V$_H$ can comprise an amino acid sequence at least 95% identical to the sequence shown in SEQ ID NO: 65 and the V$_L$ can comprise an amino acid sequence at least 95% identical to the sequence shown in SEQ ID NO: 70. In another example, the V$_H$ can comprise an amino acid sequence at least 95% identical to the sequence shown in SEQ ID NO: 65 and the V$_L$ can comprise an amino acid sequence at least 95% identical to the sequence shown in or SEQ ID NO: 75. In these examples, the V$_H$ and/or V$_L$ can be at least 96%, at least 97%, at least 98% or at least 99% identical to the recited SEQ ID NO. In another example, the V$_H$ comprises the amino acid sequence shown in SEQ ID NO: 34 or SEQ ID NO: 64. For example, the V$_H$ comprises the amino acid sequence shown in SEQ ID NO: 34. In another example, the V$_H$ comprises the amino acid sequence shown in SEQ ID NO: 64. In another example, the V$_L$ comprises the amino acid sequence shown in any one of SEQ ID NOs: 39, 44, 69 or 74. In another example, the V$_H$ comprises the amino acid sequence shown in SEQ ID NO: 34 or SEQ ID NO: 64 and the V$_L$ comprises the amino acid sequence shown in any one of SEQ ID NOs: 39, 44, 69 of 74. For example, the V$_H$ can comprise the amino acid sequence shown in SEQ ID NO: 34 and the V$_L$ can comprise the amino acid sequence shown in SEQ ID NO: 39. In another example, the V$_H$ comprises the amino acid sequence shown in SEQ ID NO: 34 and the V$_L$ comprises the amino acid sequence shown in SEQ ID NO: 44. In another example, the V$_H$ comprises the amino acid sequence shown in SEQ ID NO: 64 and the V$_L$ comprises the amino acid sequence shown in SEQ ID NO: 39. In another example, the V$_H$ comprises the amino acid sequence shown in SEQ ID NO: 64 and the V$_L$ comprises the amino acid sequence shown in SEQ ID NO: 44. In another example, the V$_H$ comprises the amino acid sequence shown in SEQ ID NO: 64 and the V$_L$ comprises the amino acid sequence shown in SEQ ID NO: 69. In another example, the V$_H$ comprises the amino acid sequence shown in SEQ ID NO: 64 and the V$_L$ comprises the amino acid sequence shown in SEQ ID NO: 74. In another example, the V$_H$ comprises the amino acid sequence shown in SEQ ID NO: 5 and the V$_L$ comprises the amino acid sequence shown in SEQ ID NO: 10 or SEQ ID NO: 15. In another example, the V$_H$ comprises the amino acid sequence shown in SEQ ID NO: 5 and the V$_L$ comprises the amino acid sequence shown in SEQ ID NO: 10. In another example, the V$_H$ comprises the amino acid sequence shown in SEQ ID NO: 5 and the V$_L$ comprises the amino acid sequence shown in SEQ ID NO: 15. In another example, the V$_H$ comprises the amino acid sequence shown in SEQ ID NO: 34 and the V$_L$ comprises the amino acid sequence shown in SEQ ID NO: 40 or SEQ ID NO: 45. In another example, the V$_H$ comprises the amino acid sequence shown in SEQ ID NO: 34 and the V$_L$ comprises the amino acid sequence shown in SEQ ID NO: 40. In another example, the V$_H$ comprises the amino acid sequence shown in SEQ ID NO: 34 and the V$_L$ comprises the amino acid sequence shown in SEQ ID NO: 10 or SEQ ID NO: 45. In another example, the V$_H$ comprises the amino acid sequence shown in SEQ ID NO: 65 and the V$_L$ comprises the amino acid sequence shown in SEQ ID NO: 70 or SEQ ID NO: 75. In another example, the V$_H$ comprises the amino acid sequence shown in SEQ ID NO: 65 and the V$_L$ comprises the amino acid sequence shown in SEQ ID NO: 70. In another example, the V$_H$ comprises the amino acid sequence shown in SEQ ID NO: 65 and the V$_L$ comprises the amino acid sequence shown in SEQ ID NO: 75.

In an example, above referenced binding proteins are antibodies. For example, the present disclosure encompasses an antibody having an above referenced combination of CDRs. For example, an antibody of the disclosure can comprise a heavy chain variable region (V$_H$) having a CDR 1 as shown in SEQ ID NO: 1, a CDR2 as shown in SEQ ID NO: 2 and a CDR3 as shown in SEQ ID NO: 3. In another example, the antibody comprises a light chain variable region (V$_L$) having a CDR1 as shown in SEQ ID NO: 6, a CDR2 as shown in SEQ ID NO: 7 and a CDR3 as shown in SEQ ID NO: 8 or SEQ ID NO: 13. In another example, the antibody comprises a light chain variable region (V$_L$) having a CDR1 as shown in SEQ ID NO: 6, a CDR2 as shown in SEQ ID NO: 7 and a CDR3 as shown in SEQ ID NO: 8. In another example, the antibody comprises a light chain variable region (V$_L$) having a CDR1 as shown in SEQ ID NO: 6, a CDR2 as shown in SEQ ID NO: 7 and a CDR3 as shown in SEQ ID NO: 13. Accordingly, in another example, the antibody comprises a V$_H$ having a CDR 1 as shown in SEQ ID NO: 1, a CDR2 as shown in SEQ ID NO: 2 and a CDR3 as shown in SEQ ID NO: 3 and a V$_L$ having a CDR1 as shown in SEQ ID NO: 6, a CDR2 as shown in SEQ ID NO: 7 and a CDR3 as shown in SEQ ID NO: 8. In another example, the antibody comprises a V$_H$ having a CDR 1 as shown in SEQ ID NO: 1, a CDR2 as shown in SEQ ID NO: 2 and a CDR3 as shown in SEQ ID NO: 3 and a V$_L$ having a CDR1 as shown in SEQ ID NO: 6, a CDR2 as shown in SEQ ID NO: 7 and a CDR3 as shown in SEQ ID NO: 13. In an embodiment of these examples, the antibody binds LMA isotype 2 and isotype 3.

In another example, binding proteins encompassed by the present disclosure can comprise the CDRs of above exemplified V$_H$ and V$_L$ combinations. In an example, the CDRs are defined using Kabat. In another example, the CDRs are defined using IMGT.

Referring to binding proteins having an above referenced % sequence identity, in various examples, binding proteins encompassed by the present disclosure can comprise at least one, at least two, at least three, at least four or at least five amino acid substitutions compared with the referenced sequence identifier number. Exemplary substitutions include conservative amino acid substitutions such as those described below in Table A.

TABLE A

| Exemplary substitutions. | |
| --- | --- |
| Original Residue | Exemplary Substitutions |
| Arg (R) | Lys (K) |
| Glu (E) | Asp (D) |
| Ile (I) | Leu (L); Val (V); Ala (A) |
| Leu (L) | Ile (I); Val (V); Met (M); Ala (A); Phe (F) |
| Lys (K) | Arg (R) |

The term "4G7" is used in the context of the present disclosure to refer to a monoclonal antibody to human free lambda light chain that binds an epitope comprising an amino acid sequences shown in:

SEQ ID NO: 91 (KADGSPVK) and 93 (SHR) (isotype 1);
SEQ ID NO: 92 (KADSSPVK) and 93 (SHR) (isotype 2); or
SEQ ID NO: 92 (KADSSPVK) and 94 (SHK) (isotype 3), 4G7 is commercially available from various suppliers (e.g. Abcam, Cambridge, United Kingdom, #ab54380; Yamasa Corporation, Choshi, Japan, #7642).

In an example, an anti-LMA binding protein encompassed by the present disclosure can bind the same epitope as 4G7. For example, an anti-LMA binding protein encompassed by the present disclosure can bind an epitope comprising an amino acid sequence shown in:

SEQ ID NO: 91 and 93 (lambda isotype 1);
SEQ ID NO: 92 and 93 (lambda isotype 2); or
SEQ ID NO: 92 and 94 (lambda isotype 3).

In another example, an anti-LMA binding protein encompassed by the present disclosure binds an epitope comprising an amino acid sequence shown in:
SEQ ID NO: 91 and 93 (lambda isotype 1);
SEQ ID NO: 92 and 93 (lambda isotype 2); or
SEQ ID NO: 92 and 94 (lambda isotype 3), and does not bind to soluble lambda-light chain.

In another example, the binding protein binds SEQ ID NO: 92 and 93 (lambda isotype 2) and SEQ ID NO: 92 and 94 (lambda isotype 3).

Various lambda light chain isotypes have been reported and these isotypes are defined by amino acid variances in the constant region of the molecule.

Lambda light chain isotypes are expressed at varying frequencies. For example, in subjects with multiple myeloma, about 14% express isotype 1, about 64% express isotype 2 and about 23% express isotype 3. Accordingly, in some examples, it may be desirable to administer an antibody according to the present disclosure which binds one or more or all lambda light chain isotypes. In an example, the binding protein binds lambda isotype 2 and isotype 3. In an example, the binding protein does not bind to isotype 1.

In another example, the binding protein has improved manufacturability compared to 4G7.

Improved manufacturability encompasses post translational modifications or increased chemical stability relating to reduced numbers of deamidation sites, aspartate isomerization sites, oxidation sites such as methionine and tryptophan, free-cysteine thiol groups, N & O-glycosylation sites, the presence of C-terminal lysine and/or isoelectric point.

In an example, the binding protein comprises less asparagine in the $V_H$ and/or $V_L$ compared with 4G7.

In an example, the binding protein comprises less methionine in the $V_H$ and/or $V_L$ compared with 4G7.

In an example, the binding protein comprises less tryptophan in the $V_H$ and/or $V_L$ compared with 4G7.

In an example, the binding protein comprises less aspartic acid in the $V_H$ and/or $V_L$ compared with 4G7.

In an example, the physical stability of the binding protein is greater than 4G7.

Physical stability can include propensity for aggregation in solution. The term "aggregation" is used in the context of the present disclosure to refer to protein self-association, which can occur in multiple environments, from cell culture and fermentation, to isolation, purification and formulation processes. For example, the term "aggregation" can be used when describing the formation of inclusions; the accumulation of protein in "insoluble" fractions following cell fractionation; the appearance of turbidity, protein precipitation or formation of particles in samples; or the formation of small soluble oligomers amongst others.

Accordingly, in the above referenced examples, the physical stability of a binding protein can be based on its physical stability in solution, wherein precipitation of the binding protein from solution indicates that the binding protein has become unstable. To assess physical stability, solutions comprising a binding protein according to the present disclosure or 4G7 can be incubated at 4° C. and assessed visually for precipitation at two weeks, four weeks, 12 weeks, six months and 12 months.

In another example, the binding protein has reduced immunogenicity in a human subject compared to 4G7. For example, a binding protein can have reduced immunogenicity compared to 4G7 when immunogenicity is measure via enzyme-linked immunosorbent assay (ELISA). In another example, a binding protein can have reduced immunogenicity compared to 4G7 when immunogenicity is measure via Surface Plasmon Resonance.

In another example, the binding protein has higher specificity for LMA than 4G7.

In another example, the binding protein has lower cross-reactivity (i.e. the ability of a binding protein to react with similar antigenic sites on different proteins) compared to 4G7. In this example, cross-reactivity of binding proteins can be measured using various methods. In an example, cross-reactivity is assessed via ELISA.

In another example, the binding protein has higher binding affinity for LMA than 4G7.

In another example, the binding protein has a higher binding affinity for LMA relative to light chain than 4G7.

In the above referenced examples, the affinity of a binding protein for LMA can be measured using various methods. In an example, the dissociation constant ($K_D$) or association constant ($K_A$) or equilibrium constant ($K_D$) of a binding protein for LMA is determined. These constants for a binding protein are, in one example, measured by a radiolabelled or fluorescently-labelled LMA-binding assay. This assay equilibrates the binding protein with a minimal concentration of labelled LMA in the presence of a titration series of unlabelled LMA. Following washing to remove unbound LMA, the amount of label is determined.

Affinity measurements can be determined by standard methodology for antibody reactions, for example, immunoassays, surface plasmon resonance (SPR) (Rich and Myszka *Curr. Opin. Biotechnol* 11:54, 2000; Englebienne *Analyst*. 123: 1599, 1998), isothermal titration calorimetry (ITC) or other kinetic interaction assays known in the art.

In one example, the constants are measured by using surface plasmon resonance assays, e.g., using BIAcore surface plasmon resonance (BIAcore, Inc., Piscataway, N.J.) with immobilized LMA. Exemplary SPR methods are described in U.S. Pat. No. 7,229,619.

In the other examples, the affinity of a binding protein for LMA can be measured using Isothermal Titration Microcalorimetry.

Binding Protein Production

Recombinant Expression

In one example, a binding protein as described herein is a peptide or polypeptide (e.g., is an antibody or antigen binding fragment thereof). In one example, the binding protein is recombinant.

In the case of a recombinant peptide or polypeptide, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce immunoglobulin or antibody protein.

Suitable molecular cloning techniques are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or 5,530,101.

Following isolation, the nucleic acid is inserted operably linked to a promoter in an expression construct or expression vector for further cloning (amplification of the DNA) or for expression in a cell-free system or in cells. Thus, another example of the disclosure provides an expression construct that comprises an isolated nucleic acid of the disclosure and one or more additional nucleotide sequences. Suitably, the expression construct is in the form of, or comprises genetic components of, a plasmid, bacteriophage, a cosmid, a yeast or bacterial artificial chromosome as are understood in the art. Expression constructs may be suitable for maintenance and propagation of the isolated nucleic acid in bacteria or other host cells, for manipulation by recombinant DNA technology and/or for expression of the nucleic acid or a binding protein of the disclosure.

Many vectors for expression in cells are available. The vector components generally include, but are not limited to, one or more of the following: a signal sequence, a sequence encoding the binding protein (e.g., derived from the information provided herein), an enhancer element, a promoter, and a transcription termination sequence. Exemplary signal sequences include prokaryotic secretion signals (e.g., pelB, alkaline phosphatase, penicillinase, lpp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin or antibody promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., Wis., USA) amongst others.

The host cells used to produce the binding protein (e.g., antibody or antigen binding fragment) may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

The skilled artisan will understand from the foregoing description that the present disclosure also provides an isolated nucleic acid encoding a binding protein (e.g., a peptide or polypeptide binding protein or an antibody or antigen binding fragment thereof) of the present disclosure.

The present disclosure also provides an expression construct comprising an isolated nucleic acid of the disclosure operably linked to a promoter. In one example, the expression construct is an expression vector.

In one example, the expression construct of the disclosure comprises a nucleic acid encoding a polypeptide (e.g., comprising a $V_H$) operably linked to a promoter and a nucleic acid encoding another polypeptide (e.g., comprising a $V_L$) operably linked to a promoter.

The disclosure also provides a host cell comprising an expression construct according to the present disclosure.

The present disclosure also provides an isolated cell expressing a binding protein of the disclosure or a recombinant cell genetically-modified to express the binding protein.

Isolation of Proteins

Methods for purifying binding proteins according to the present disclosure are known in the art. Where a peptide or polypeptide is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Binding protein prepared from cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

Conjugates

In one example, a binding protein of the present disclosure is conjugated to another compound. The binding protein can be directly or indirectly bound to the compound (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal or quantum dot), a therapeutic compound (e.g., a chemotherapeutic or an anti-inflammatory), a colloid (e.g., gold), a toxin (e.g., ricin or tetanus toxoid), a nucleic acid, an agent that increases the half-life of the compound in a subject (e.g., polyethylene glycol or other water soluble polymer having this activity) and mixtures thereof.

Methods for attaching a drug or other small molecule pharmaceutical to an antibody are well known and can include use of bifunctional chemical linkers such as N-succinimidyl (4-iodoacetyl)-aminobenzoate; sulfosuccinimidyl (4-iodoacetyl)-aminobenzoate; 4-succinimidyl-oxycarbonyl-(2-pyridyldithio) toluene; sulfosuccinimidyl-6-[α-methyl-∀-(pyridyldithiol)-toluamido]hexanoate; N-succinimidyl-3-(-2-pyridyldithio)-proprionate; succinimidyl-6-[3 (-(-2-pyridyldithio)-proprionamido]hexanoate; sulfosuccinimidyl-6-[3 (-(-2-pyridyldithio)-propionamido]

hexanoate; 3-(2-pyridyldithio)-propionyl hydrazide, Ellman's reagent, dichlorotriazinic acid, S-(2-thiopyridyl)-L-cysteine, and the like. Further bifunctional linking molecules are discussed in, for example, U.S. Pat. Nos. 5,349,066, 5,618,528, 4,569,789, 4,952,394, and 5,137,877.

The linker can be cleavable or noncleavable. Highly stable linkers can reduce the amount of payload that falls off in circulation, thus improving the safety profile, and ensuring that more of the payload arrives at the target cell. Linkers can be based on chemical motifs including disulfides, hydrazones or peptides (cleavable), or thioethers (noncleavable) and control the distribution and delivery of the active agent to the target cell. Cleavable and noncleavable types of linkers have been proven to be safe in preclinical and clinical trials (see, e.g., Brentuximab vedotin which includes an enzyme-sensitive linker cleavable by cathepsin; and Trastuzumab emtansine, which includes a stable, non-cleavable linker). In an example, the linker is a peptide linker cleavable by Edman degredation (Bçchor, et al., *Molecular diversity*, 17 (3): 605-11 (2013)).

In an example, the binding protein is conjugated to nanoparticles or microparticles (for example as reviewed in Kogan et al., *Nanomedicine (Lond)*. 2: 287-306, 2007). The nanoparticles may be metallic nanoparticles. The particles can be polymeric particles, liposomes, micelles, microbubbles, and other carriers and delivery vehicles known in the art.

Some exemplary compounds that can be conjugated to a binding protein of the present disclosure are listed in Table B.

TABLE B

Compounds useful in conjugation.

| Group | Detail |
| --- | --- |
| Radioisotopes (either directly or indirectly) | $^{123}$I, $^{125}$I, $^{130}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Re, $^{203}$Pb, $^{64}$Cu, $^{105}$Rh, $^{198}$Au, $^{199}$Ag or $^{177}$Lu |
| Half-life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Chemotherapeutics | Taxol<br>5-FU<br>Doxorubicin<br>Idarubicin |

In one example, a binding protein of the disclosure is conjugated to a chemotherapy agent.

Compositions

Suitably, in compositions or methods for administration of a binding protein according to the present disclosure to a subject, the binding protein is combined with a pharmaceutically acceptable carrier as is understood in the art. In one example, the present disclosure provides a composition (e.g., a pharmaceutical composition) comprising a binding protein of the disclosure combined with a pharmaceutically acceptable carrier. In another example, the disclosure provides a kit comprising a pharmaceutically acceptable carrier suitable for combining or mixing with a binding protein disclosed herein prior to administration to the subject. In this example, the kit may further comprise instructions for use.

In general terms, "carrier" is used to refer to a solid or liquid filler, binder, diluent, encapsulating substance, emulsifier, wetting agent, solvent, suspending agent, coating or lubricant that may be safely administered to a subject, e.g., a human subject. Depending upon the particular route of administration, a variety of acceptable carriers, known in the art may be used, as for example described in Remington's Pharmaceutical Sciences (Mack Publishing Co. N.J. USA, 1991).

For example, suitable carriers may be selected from a group including sugars (e.g. sucrose, maltose, trehalose, glucose), starches, cellulose and its derivatives, malt, gelatine, talc, calcium sulfate, oils inclusive of vegetable oils, synthetic oils and synthetic mono- or di-glycerides, lower alcohols, polyols, alginic acid, phosphate buffered solutions, lubricants such as sodium or magnesium stearate, isotonic saline and pyrogen-free water. In an example, the carrier is not $H_2O$.

In an example, the carrier is compatible with, or suitable for, parenteral administration. Parenteral administration includes any route of administration that is not through the alimentary canal. Examples of parenteral administration include injection, infusion and the like. Examples of administration by injection include intravenous, intra-arterial, intramuscular and subcutaneous injection. In another example, compositions can be delivered via a depot or slow-release formulation which may be delivered intradermally, intramuscularly or subcutaneously.

In an example, an LMA binding protein disclosed herein is utilized for detecting site or sites of cancer. The method typically including administering to a subject in need thereof an effective amount an agent that is detectable using diagnostic imaging or nuclear medicine techniques, and detecting the agent. In such methods, the agent is typically conjugated to the LMA binding protein or encapsulated in a delivery vehicle conjugated with the LMA binding protein. The diagnostic imaging or nuclear medicine technique can be, for example, PET-CT, bone scan, MRI, CT, echocardiography, ultrasound, and x-ray.

In an example, binding proteins and compositions comprising the same can be used in the manufacture of a medicament for the treatment of a condition characterised by aberrant proliferation of LMA-expressing cells such as LMA-expressing cancer. In another example, the present disclosure relates to a binding protein or compositions comprising the same for use in the treatment of a condition. Examples of conditions to be treated are discussed below.

Conditions to be Treated

In an example, the present disclosure encompasses methods of treating an LMA-expressing cancer, the methods comprising administering an anti-LMA binding protein defined herein. For example, the present disclosure encompasses methods of treating B-cell malignancy wherein the malignant B-cells express LMA. In another example, the present disclosure encompasses methods of treating multiple myeloma and related pathologies. The terms "multiple myeloma" or "myeloma" are used in the context of the present disclosure to refer to cancer of plasma cells. In the context of the present disclosure, these terms encompasses secretory myeloma, non-secretory myeloma, light chain only myeloma, smouldering myeloma and related pathologies. Exemplary related pathologies include plasmacytoma, amyloidosis, monoclonal gammopathy of undetermined significance. In an example, the multiple myeloma is lambda-type multiple myeloma.

Accordingly, in an example, the present disclosure encompasses methods of treating amyloidosis. In an example, such methods comprise administering a binding protein disclosed herein with a high affinity for free lambda light chain. For example, a binding protein comprising a $V_H$ having a CDR 1 as shown in SEQ ID NO: 31, a CDR2 as shown in SEQ ID NO: 32 and a CDR3 as shown in SEQ ID NO: 33 and a $V_L$ having a CDR 1 as shown in SEQ ID NO: 36, a CDR2 as shown in SEQ ID NO: 37 and a CDR3 as shown in SEQ ID NO: 38 can be administered. In another example, a binding protein having a $V_H$ comprising an amino acid sequence shown in SEQ ID NO: 34 and a $V_L$ having an amino acid sequence shown in SEQ ID NO: 39 can be administered. In another example, a binding protein comprising a $V_H$ having a CDR 1 as shown in SEQ ID NO: 66, a CDR2 as shown in SEQ ID NO: 67 and a CDR3 as shown in SEQ ID NO: 68 and a $V_L$ having a CDR 1 as shown in SEQ ID NO: 71, a CDR2 as shown in SEQ ID NO: 72 and a CDR3 as shown in SEQ ID NO: 73 can be administered. In another example, a binding protein having a $V_H$ comprising an amino acid sequence shown in SEQ ID NO: 64 and a $V_L$ having an amino acid sequence shown in SEQ ID NO: 74 can be administered. In another example, a binding protein comprising a $V_H$ having a CDR 1 as shown in SEQ ID NO: 61, a CDR2 as shown in SEQ ID NO: 62 and a CDR3 as shown in SEQ ID NO: 63 and a $V_L$ having a CDR 1 as shown in SEQ ID NO: 66, a CDR2 as shown in SEQ ID NO: 67 and a CDR3 as shown in SEQ ID NO: 68 can be administered.

Subjects with multiple myeloma can be characterised into various subject populations. Exemplary populations are described in (Rajkumar et al. 2011).

In an example, a subjects multiple myeloma can be characterised as progressive disease (Rajkumar et al. 2011). Put another way, the methods of the present disclosure relate to the treatment of progressive multiple myeloma in a subject. Exemplary indicators of "progressive disease" include an increase of about 25% from the lowest response value in any one of the following: Serum M-component (absolute increase > or equal to 0.5 g/dL) and/or Urine M-component (absolute increase must be > or equal to 200 mg/24 hr. Other exemplary indicators include definite development of new bone lesions or soft tissue plasmacytomas or definite increase in the size of existing bone lesions or soft tissue plasmacytomas; development of hypercalcemia (corrected serum calcium >11.5 mg/dL) that can be attributed solely to the multiple myeloma. In an example, the subjects multiple myeloma has relapsed and is characterised as progressive disease. In this example, the subjects multiple myeloma can also be refractory to therapy.

In an example, the subjects multiple myeloma has relapsed. "Relapsed myeloma" is used to refer to previously treated myeloma that progresses and requires the initiation of salvage therapy but does not meet criteria for either "primary refractory myeloma".

In another example, the subject has primary refractory myeloma. "Primary refractory myeloma" is used to refer to disease that is nonresponsive in patients who have never achieved a minimal response or better with any therapy.

In another example, the subject has refractory myeloma. The term "refractory myeloma" is used to refer to disease that is nonresponsive while on primary or salvage therapy, or progresses within 60 days of last therapy. In an example, a subjects multiple myeloma is refractory to an anti-cancer therapy. The term "refractory" is used in this context to refer to a line of anti-cancer therapy that is no longer therapeutically effective against a subject's multiple myeloma. For example, a subject treated by the methods of the present disclosure can be refractory to at least one proteasome inhibitor. A "line of therapy" is defined as one or more cycles of a planned treatment program. This may consist of one or more planned cycles of single-agent therapy or combination therapy, as well as a sequence of treatments administered in a planned manner. For example, a planned treatment approach of induction therapy followed by autologous stem cell transplantation, followed by maintenance is considered one line of therapy.

In another example, subjects are refractory to at least two prior lines of therapy. In another example, a subject may be refractory to at least three, at least four, at least five, at least six prior lines of therapy.

In another example, the subject has relapsed and refractory myeloma. "Relapsed and refractory myeloma" is used to refer to disease that is nonresponsive while on salvage therapy, or progresses within 60 days of last therapy in patients who have achieved minimal response (MR) or better at some point previously before then progressing in their disease course.

In an example, the multiple myeloma treated according to the present disclosure is characterised as stable disease at the time of first administration. Put another way, subjects can be in plateau phase at the time of first administration. Exemplary criteria for stable disease can include stabilization of the M-protein without further tumour regression despite continued treatment, few or no symptoms from myeloma and/or no blood transfusion requirement (Blade et al. 1998).

In another example, the methods of the present disclosure can be used to treat B cell lymphoma and macroglobulinemia.

In another example, the methods of the present disclosure can be used to treat POEMS. As used herein "POEMS syndrome" is a rare blood disorder that damages the nerves and affects many other parts of the body. "POEMS" stands for these signs and symptoms: Polyneuropathy: numbness, tingling and weakness in the legs and over time in the hands and difficulty breathing; Organomegaly: enlarged spleen, liver or lymph nodes; Endocrinopathy: abnormal hormone levels that can result in underactive thyroid (hyperthyroidism), diabetes, sexual problems, fatigue, swelling in the limbs and problems with metabolism and other essential functions; Monoclonal plasma-proliferative disorder: abnormal bone marrow cells (plasma cells) that produce a protein that can be found in the bloodstream; Skin changes: more color than normal on the skin, possibly thicker skin and increased facial and/or leg hair.

In another example, binding proteins defined herein can be administered to a subject to treat an autoimmune disorder. In an example, the autoimmune disorder is characterised by aberrant proliferation of plasma cell precursors expressing LMA as membrane free light chain (mFLC). For example, binding proteins defined herein can be administered to a subject to treat an autoimmune disorder such as rheumatoid arthritis, systemic lupus erythematosus, diabetes mellitus, multiple sclerosis, Crohn's disease, immune thrombocytopenic purpura, pemphigis vulgaris, autoimmune urticaria, celiac disease, dermatitis herpetiformis, acute rhematic fever, Grave's disease, myasthenic gravis, Sjogren's syndrome, Goodpasture's syndrome, poststreptococcal glomerulonephritis, contact dermatitis, autoimmune thyroiditis, Hashimoto's thyroiditis, Addison's disease, autoimmune haemo lytic anaemia, pernicious anaemia, vasculitis caused by anti-neutrophil cytoplasmic antibodies (ANCA), polyarteritis nodosa, autoimmune hepatitis, and primary biliary cirrhosis. For example, the methods of the present disclosure can be used to treat rheumatoid arthritis, systemic lupus erythematosus, diabetes mellitus, and multiple sclerosis. Accordingly, in an example, the methods of the present disclosure can be used to treat rheumatoid arthritis. In another example, the present disclosure can be used to treat systemic lupus erythematosus. In another example, binding proteins according to the present disclosure can be used to treat diabetes mellitus. In another example, binding proteins according to the present disclosure can be used to treat multiple sclerosis.

In another example, the binding proteins according to the present disclosure can be used to reduce lambda free light chain levels in a subject (i.e. reduce the amount of lambda light chain in a subject that is not expressed on the cell membrane, e.g. lambda light chain in serum). Such methods comprise administering a binding protein disclosed herein with a high affinity for free lambda light chain. For example, a binding protein comprising a $V_H$ having a CDR 1 as shown in SEQ ID NO: 31, a CDR2 as shown in SEQ ID NO: 32 and a CDR3 as shown in SEQ ID NO: 33 and a $V_L$ having a CDR 1 as shown in SEQ ID NO: 36, a CDR2 as shown in SEQ ID NO: 37 and a CDR3 as shown in SEQ ID NO: 38 can be administered. In another example, a binding protein having a $V_H$ comprising an amino acid sequence shown in SEQ ID NO: 34 and a $V_L$ having an amino acid sequence shown in SEQ ID NO: 39 can be administered. In another example, a binding protein comprising a $V_H$ having a CDR 1 as shown in SEQ ID NO: 66, a CDR2 as shown in SEQ ID NO: 67 and a CDR3 as shown in SEQ ID NO: 68 and a $V_L$ having a CDR 1 as shown in SEQ ID NO: 71, a CDR2 as shown in SEQ ID NO: 72 and a CDR3 as shown in SEQ ID NO: 73 can be administered. In another example, a binding protein having a $V_H$ comprising an amino acid sequence shown in SEQ ID NO: 64 and a $V_L$ having an amino acid sequence shown in SEQ ID NO: 74 can be administered. In another example, a binding protein comprising a $V_H$ having a CDR 1 as shown in SEQ ID NO: 61, a CDR2 as shown in SEQ ID NO: 62 and a CDR3 as shown in SEQ ID NO: 63 and a $V_L$ having a CDR 1 as shown in SEQ ID NO: 66, a CDR2 as shown in SEQ ID NO: 67 and a CDR3 as shown in SEQ ID NO: 68 can be administered.

In another example, the methods of the present disclosure encompass treating an LMA-expressing cancer or other disorder disclosed herein by administering a binding protein of the present disclosure with a high affinity for free lambda light chain in combination with a binding protein of the present disclosure with a low affinity for free lambda light chain. For example, a binding protein having a $V_H$ comprising an amino acid sequence shown in SEQ ID NO: 64 and a $V_L$ having an amino acid sequence shown in SEQ ID NO: 74 can be administered in combination with a binding protein having a $V_H$ comprising an amino acid sequence shown in SEQ ID NO: 4 and a $V_L$ having an amino acid sequence shown in SEQ ID NO: 9. In another example, a binding protein having a $V_H$ comprising an amino acid sequence shown in SEQ ID NO: 64 and a $V_L$ having an amino acid sequence shown in SEQ ID NO: 74 can be administered in combination with a binding protein having a $V_H$ comprising an amino acid sequence shown in SEQ ID NO: 4 and a $V_L$ having an amino acid sequence shown in SEQ ID NO: 9.

Antibodies administered in combination as part of performing the methods of the present disclosure may be administered simultaneously or sequentially.

EXAMPLES

Example 1: Lambda Myeloma Antigen (LMA) on Lambda Multiple Myeloma Cells

To determine the presence of lambda myeloma antigen (LMA) on the surface of lambda multiple myeloma cells, murine monoclonal antibody 4G7 raised against lambda Bence Jones Proteins (BJP) was used in ELISA, Surface Plasmon Resonance (SPR) and Western Blot assays. Mouse monoclonal antibody 4G7 demonstrated pan reactivity against all free lambda light chain BJP and a range of lambda human multiple myeloma cell lines which encompassed the 3 dominant lambda light chain isotypes compared to mouse monoclonal antibody 3D12 (Tables 1 and 2). Its interaction could be inhibited by lambda free light chains and not IgG/lambda, demonstrating the presence of lambda light chains on the cell surface of the lambda human multiple myeloma cell line RPMI8226. 4G7 also detected LMA on lambda multiple myeloma patient derived bone marrow mononuclear cell populations which were positive for CD38 and CD138 as determined by flow cytometric analysis (Table 3). Epitope excision experiments identified two peptides as components of the 4G7 monoclonal antibody epitope on lambda multiple myeloma cell line (FIG. 1).

TABLE 1

Murine monoclonal antibody 4G7 binds all lambda light chains in SPR assays

| Lambda BJP | Biocore Response (RU) | | | |
|---|---|---|---|---|
| | 4G7 | | 3D12 | |
| Lam034 | 298 | +++ | 16 | – |
| Lam134c | 161 | ++ | 11 | – |
| Lam788a | 49 | + | 15 | – |
| Lam885 | 243 | +++ | 350 | +++ |
| Lam893c | 110 | ++ | 150 | ++ |
| MOS | –5 | – | 14 | – |
| IgGlambda | 30 | –/+ | 13 | – |

TABLE 2

Murine monoclonal antibody 4G7 binds all lambda light chains in ELISA assays

| Lambda BJP | ELISA Response | | | |
|---|---|---|---|---|
| | 4G7 | | 3D12 | |
| Lam034 | 1.416 | +++ | –0.016 | – |
| Lam134c | 1.328 | +++ | –0.024 | – |
| Lam788a | 1.399 | +++ | –0.027 | – |
| Lam885 | 1.326 | +++ | 0.890 | ++ |
| Lam893c | 1.327 | +++ | 0.509 | + |
| MOS | 1.277 | +++ | 0.001 | – |
| IgGlambda | 0.532 | + | 0.117 | –/+ |
| κBJP | 0.000 | – | –0.011 | – |

TABLE 3

Murine monoclonal antibody 4G7 detects LMA on primary bone marrow cells from lambda multiple myeloma patients.

| Patient | Isotype | Free light chain (mg/L) | % PC | LMA | Comments |
|---|---|---|---|---|---|
| 1 | NA | NA | 6 | ND | CD45+CD38+ cells detected |

TABLE 3-continued

Murine monoclonal antibody 4G7 detects LMA on primary bone marrow cells from lambda multiple myeloma patients.

| Patient | Isotype | Free light chain (mg/L) | % PC | LMA | Comments |
|---|---|---|---|---|---|
| 2 | NA | 142 | 30 | + | Stained for LMA only |
| 3 | LC MM | 1372.5 | 18 | + | CD45−CD38+ cells detected |
| 4 | G | NA | 6 | ND | CD45−CD38+CD138+ cells detected |
| 5 | A | 61.6 | 13 | + | CD45−CD38+CD138+ cells detected |

Abbreviations. NA: not available; ND: not detected; FLC: free light chain; % PC: percentage bone marrow plasma.

Example 2: Generation of Human Anti-LMA Antibodies

HuMAb-Mice (Medarex) were immunized with Ig free lambda-light chains and lambda myeloma antigen (LMA) positive cell lines. Human anti-LMA antibodies were screened for binding to Ig free lambda-light chains and Ig associated lambda-light chains using ELISA to identify LMA specific candidates. Human anti-LMA antibodies were purified and characterized by binding to LMA positive cell lines using flow cytometry and affinity for Ig free lambda-light chains using Surface Plasmon Resonance (SPR) analysis. Human anti-LMA antibody candidates identified were 1A11, 7F11, 10B3, 18E8, 18E11, 18F9.

Example 3: Human Anti-LMA Antibodies Bind Lambda Light Chains

To determine the binding affinity of anti-LMA antibodies to lambda-light chain, Surface Plasmon Resonance (SPR) experiments were performed. Anti-human Ig light chain was immobilised on BIACore CM5 chips and used to capture the human anti-LMA antibody candidates (20 µg/mL). The tested lambda-light chains were injected (20 µL/min) following the candidate capture and SPR was determined (relative units: RU).

Figure 2B:
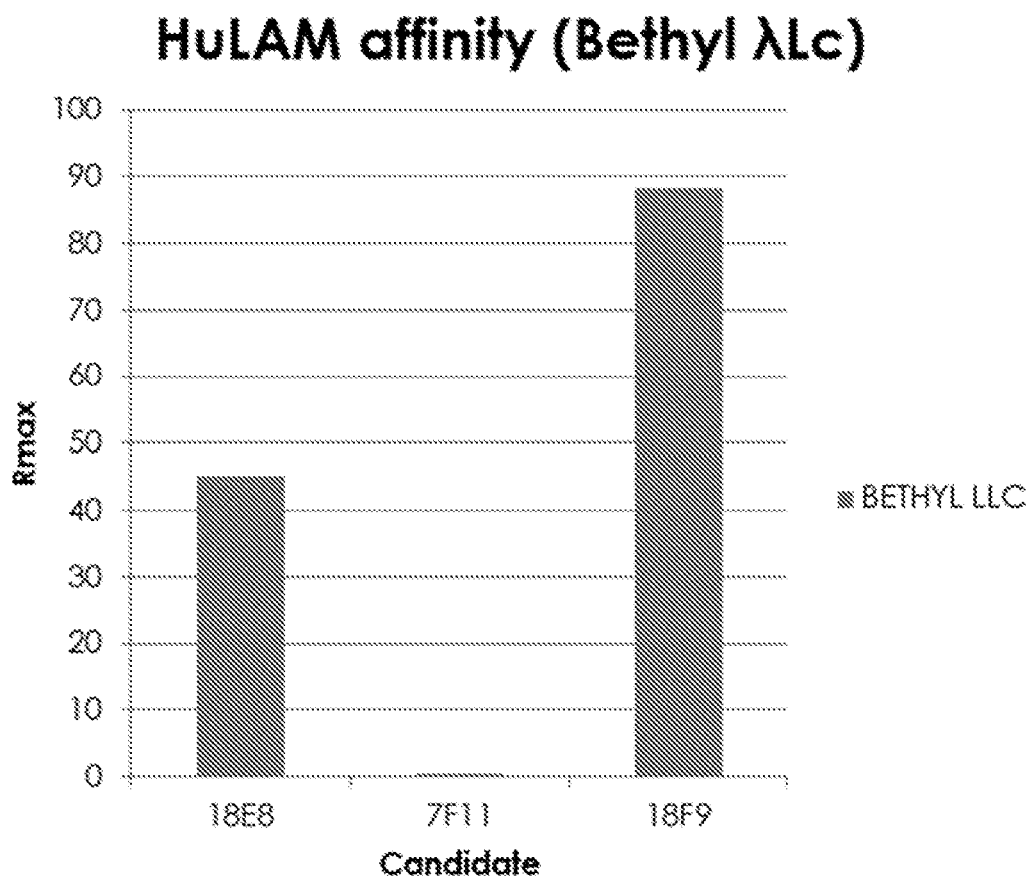

Human anti-LMA antibodies (clones 1A11, 7F11, 10B3, 18E8, 18E11 and 18F9) demonstrated high and selective affinity to purified lambda-light chains BJP but not κBJP (KAP960M) (FIG. 2A), cynomologus monkey lambda-light chains (CYNO1, CYNO3), and supernatant from lambda-light chain transfected HEK cells, LP-1 lambda-light chain isolate (LP-1 ISO) and RPMI-8226 lambda-light chain isolate (RPMI-8226 ISO) (FIG. 3). Similarly, human anti-LMA antibodies (6A1, 13H3 and 4A1) demonstrated high and selective affinity to human multiple myeloma cell lines expressing lambda-light chain isotypes and not to kappa-light chain expressing JJN3 cell line (FIG. 4) while clones 18E8, 7F11 and 18F9 demonstrated selective affinity to commercial lambda-light chain (Bethyl) (FIG. 2B).

Human anti-LMA antibody 7F11 demonstrated lower selective affinity to purified lambda-light chains BJP compared to other clones tested (FIG. 2A, 2B) and demonstrated low affinity to cynomologus monkey lambda-light chains (CYNO1, CYNO3; FIG. 3) and supernatant from lambda-light chain transfected HEK cells, LP-1 lambda-light chain isolate (LP-1 ISO) and RPMI-8226 lambda-light chain isolate (RPMI-8226 ISO) (FIG. 4).

Example 4: Human Anti-LMA Antibodies Bind LMA Positive Human Myeloma Cell Lines To determine the binding of human anti-LMA antibodies to human myeloma cell lines expressing LMA of divergent lambda isotypes, flow cytometric analysis was performed.

Figure 5B:
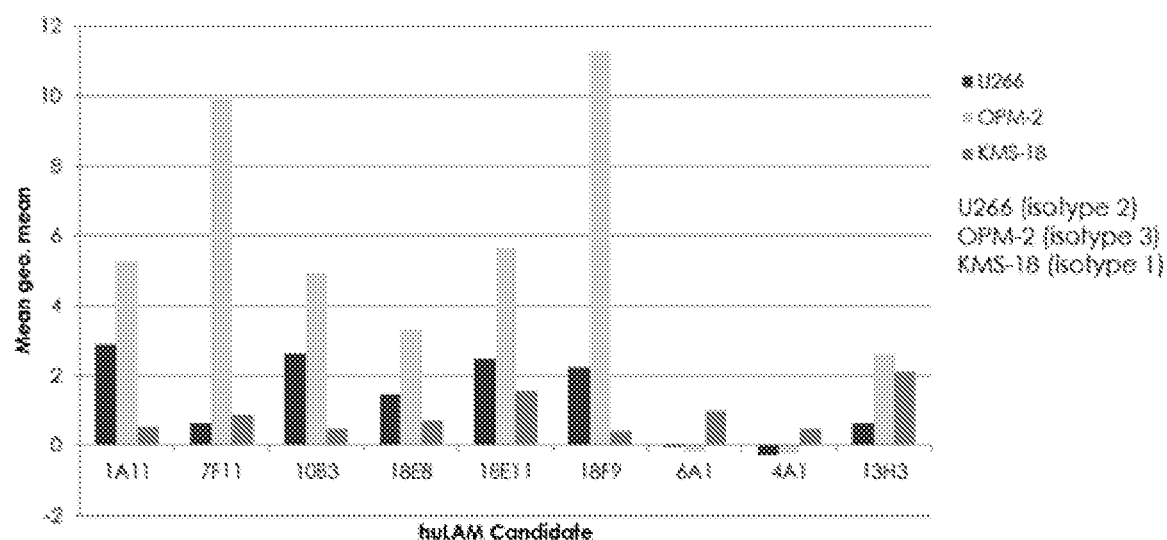

Human myeloma cell lines ($5 \times 10^5$ cells) were stained with a solution of human anti-LMA antibody (50 µg/mL) or mouse anti-LMA antibody 4G7. Human anti-LMA antibodies (1A11, 7F11, 10B3, 18E8, 18E11 and 18F9) demonstrated selective staining of all tested human myeloma cell lines (RPMI-8226 (lambda isotype 2), U266 (lambda isotype 2), JJN3 (kappa), OPM-2 (lambda isotype 3)), did not (or weakly) stained JJN3 (kappa) cell line (FIG. 5A) and demonstrated weak staining against KMS-18 (lambda isotype 1) (FIG. 5B). Human anti-LMA antibodies (6A1, 4A1 and 13H3) demonstrated low staining of all tested LMA positive human myeloma cell lines.

Example 5: Antibody Dependent Cellular Cytotoxicity (ADCC)

Peripheral blood mononuclear cell (PMBC) preparations or specific cell populations such as natural killer (NK) cells or monocytes contained with PMBC preparations were analysed in ADCC assays. Blood was overlaid on Ficoll, the gradient was centrifuged and PBMCs were collected from the interface of the gradient.

Specific cell populations were isolated from PMBC preparations generated using magnetically labelled antibody preparations (Miltenyi Biotec, Germany) to deplete undesired cells. Effector and target cells were mixed and incubated in RPMI supplemented with 10% fetal calf serum at 37° C. for 16 hours. Degree of cell lysis was determined by measuring the level of intracellular lactate dehydrogenase (LDH) released (CytoTox-ONE Homogenous Membrane Integrity Assay Kit; Promega, USA).

Human anti-LMA antibodies showed varying degree of effector function with clone 10B3 demonstrating the strongest ADCC amongst the antibodies tested (FIG. 6).

Example 6: Complement Dependent Cytotoxicity (CDC)

Target cells were incubated in the presence of complement (either purified or human serum containing complement) and antibody in RPMI supplemented with 10% fetal calf serum for between 30 minutes to 12 hours at 37° C. Degree of cell lysis was determined by measuring the level of intracellular lactate dehydrogenase (LDH) released (CytoTox-ONE Homogenous Membrane Integrity Assay Kit; Promega, USA). Metabolic state of cells was measured using Alamar Blue (Invitrogen, USA).

Human anti-LMA antibodies showed varying degree of effector function with clone 10B3 demonstrating the strongest CDC activity amongst the antibodies tested (FIG. 7).

Example 7: Human Anti-LMA Antibody 7F11 Selective for LMA and not Free Lambda-Light Chains Human anti-LMA antibodies 10B3 and 18E8 bind to both soluble lambda-light chains and LMA positive cells and can promote ADCC and CDC when used to target lambda expressing RPMI8226 cells (Table 5). Interestingly, human anti-LMA antibody 7F11 is selective for LMA (membrane bound light chain) and can promote ADCC and CDC when used to target lambda expressing RPMI8226 cells but does not bind to soluble lambda-light chains (Table 5). Analysis of 7F11 sequence revealed unique heavy chain CDRs compared to other human antibodies tested that bound free light chain (FIG. 8). The different binding characteristics between human anti-LMA antibodies 7F11 compared to 10B3 and 18E8 allows for their selective use to deplete free lambda light chain and/or target LMA positive cells.

TABLE 5

Human anti-LMA antibody affinity to lambda-light chains or LMA positive cells.

| Clone Name | Binds to LP-1 (λ isotype 1) | ADCC RPMI8226 (λ isotype 2) | CDC RPMI8226 (λ isotype 2) | Binds soluble λ light chains | Binds LMA+ cell lines |
|---|---|---|---|---|---|
| 10B3 | Y | Y | Y | Y | Y |
| 1A11 | Y | Y | Y | Y | Y |
| 18E8 | Y | N | Y | Y | Y |
| 18E11 | Y | Y | P | Y | Y |
| 18F9 | Y | N | Y | Y | Y |
| 7F11 | N | Y | Y | N | Y |
| 4A1 | N | P | Y | N | N |
| 6A1 | N | P | Y | N | N |
| 13H3 | N | Y | Y | Y | N |
| 13B5 | N | P | P | P | P |

Abbreviations: Y: yes, strong affinity; N: no, weak affinity; P: possible, further evaluation required.
Table 5 notes that 7F11 doesn't bind to cells that express lambda light chain isotype 1 whereas 4G7, 18E8 and 10B3 do.

Example 8: Human Anti-LMA Antibody Staining in Human Tissue

Human LP-1 (multiple myeloma) cells, JJN3 (plasma cell leukaemia), human tonsil specimens and human cerebellum specimens were contacted with 10B3 and 7F11 antibodies and antibody staining was compared against control antibody staining from HuIgG1-lambda.

LP-1 cells express LMA isotype 1. 10B3 stained LP-1 cells while 7F11 did not stain LP-1 cells. These results are consistent with the above results which show that 10B3 binds lambda isotype 1 while 7F11 does not. No staining of JJN3 cells were observed with either 10B3 or 7F11.

Tonsils are the first sites where microbial and environmental antigens are managed in the body and therefore house lymphoid cells (About 55% of lymphoid cells are B cells). Weak to strong staining of rare mononuclear cells in follicular germinal centres, interfollicular germinal centres and interfollicular areas was observed with 10B3 and 7F11 (FIG. 9 and FIG. 10; 10B3 stained human tonsil with greater affinity that 7F11). These results confirm that both 10B3 and 7F11 can bind to cells expressing LMA in humans.

Importantly, no staining of human cerebellum was observed for 10B3 or 7F11. Human cerebellum is known to be an effective control for assessing non-specific binding. The lack of staining by both 10B3 and 7F11 highlights the specificity of these antibodies for LMA and reduces the risk of non-specific binding in-vivo.

Example 9: Anti-LMA Antibody Affinity

Anti-human Fc IgG was immobilized onto a CMS sensor chip (Protein A; Fc2 was captured with antibodies and Fc1 was set as Blank). Anti-LMA antibody (7F11-$V_L$1; 10B3-$V_L$1; 10B3-$V_L$2) was flowed over the chip surface (running buffer: 1×HBS-EP+ (10 mM HEPES, 150 mM NaCl, 3 mM EDTA, 0.05% P20, pH 7.4) @ 25 degrees Celsius and binding characteristics were recorded using Biacore 8k. Assay characteristics are summarised in Table 6. Affinity measurements are shown in Table 7.

10B3-VL1 bound with high affinity to all lambda free light chain antigens. 7F11 only bound to Sigma, 134c and 788a lambda free light chain antigens but with low affinity. These findings are in keeping with example 7 which shows that 7F11 is selective for LMA and not free lambda-light chains. 10B3-VL2 didn't bind to any lambda light chains suggesting that changes to the J gene of this antibody abolished affinity for lambda free light chain.

Importantly, no binding to Kappa light chain was observed for any of the antibodies tested further confirming specificity of these antibodies for lambda light chain.

In summary, 7F11 has no/low affinity binding to soluble lambda light chains but does bind to LMA+ cell lines with isotype 2 and 3. In contrast, 10B3-VL1 binds to all soluble lambda light chains with a high affinity and binds to all LMA+ cell lines (isotypes 1, 2 and 3). 10B3-VL2 which has a different J gene to 10B3-VL1, doesn't bind to soluble lambda light chains.

TABLE 6

Assay characteristics

| Capture | |
|---|---|
| Ligand | Antibodies |
| Concentration (ug/mL) | 2 |
| Capture time (s) | 30 |
| Flow rate (μl/min) | 10 |
| Association & Dissociation | |
| Association contact time (s) | 180 |
| Dissociation contact time (s) | 600 |
| Flow rate (μl/min) | 30 |
| Sample concentrations (nM) | 3.125, 6.25, 12.5, 25, 50, 100 |
| Regeneration | 10 mM glycine pH 1.5, 30 s |

TABLE 7

Affinity measurements

| Hybridoma | Binding to Lambda Free Light Chains - $K_D$ (M) | | | | | | |
|---|---|---|---|---|---|---|---|
| Clone | MyBio | Sigma | 134c | 885 | 893c | 788a | Kappa LC |
| 7F11-VL1 | None | $1.44 \times 10^{-7}$ | $3.2 \times 10^{-7}$ | None | None | $3.63 \times 10^{-7}$ | None |
| 10B3-VL1 | $4.37 \times 10^{-11}$ | $5.22 \times 10^{-10}$ | $4.53 \times 10^{-11}$ | $7.07 \times 10^{-11}$ | $4.01 \times 10^{-11}$ | $1.1 \times 10^{-10}$ | None |
| 10B3-VL2 | None | None | None | None | None | None | None |

It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

The present application claims priority from AU 2018900534 filed 20 Feb. 2018, the entire contents of which are incorporated herein by reference.

REFERENCES

Adams et al. (1993) Cancer Res. 53:4026
Airoldi, et al. (2008) Blood, 112(3):750-759
Ausubel et al., (editors), Current Protocols in Molecular Biology, Greene Pub.
Associates and Wiley-Interscience (1988, including all updates until present)
AHo (Honegger A, Plückthun A (2001) J Mol Biol 309: 657-670
Baçhor, et al., Molecular diversity, 17 (3): 605-11 (2013)
Blade et al. 1998
Chothia (Chothia C, Lesk A M (1987), J Mal Biol 196: 901-917
Chothia, et al. (1989), Nature 342: 877-883
Gruber et al. (1994) J. Immunol.: 5368
Ed Harlow and David Lane (editors) Antibodies: A Laboratory Manual, Cold Spring Harbor Laboratory, (1988)
Hollinger et al., 1993, supra
Hu et al. (1996) Cancer Res. 56:3055
Kogan et al., *Nanomedicine* (*Lond*). 2: 287-306, 2007
Kostelny et al. (1992) J Immunol 148:1547
Kuby, J., Immunology, $3^{rd}$ Ed., W.H. Freeman & Co., New York (1998)
Lefranc, et al. (2003), Dev Comp Immunol 27: 55-77
McCartney, et al. (1995) Protein Eng. 8:301
Novotny et al., Proc Natl Acad Sci USA 88: 8646-8650, 1991
Pack and Pluckthun (1992) Biochemistry 31:1579
Pierce Catalogue and Handbook, 1994-1995 (Pierce Chemical Co., Rockford, Ill.)
Rajkumar et al. 2011
Remington's Pharmaceutical Sciences (Mack Publishing Co. N.J. USA, 1991)
Rich and Myszka *Curr. Opin. Biotechnol* 11:54, 2000; Englebienne *Analyst.* 123: 1599, 1998
Sambrook et al., Molecular Cloning: A Laboratory Manual, Cold Spring Harbor Laboratory Press (1989)
Wang, et al. (2014) Anticancer Drugs, 25(3): 282-288
Zhu et al. (1997) Protein Sci 6:781

The invention claimed is:

1. An anti-LMA binding protein having an antigen binding domain that binds to LMA, the binding protein comprising:
   a $V_H$ comprising a CDR1 as shown in SEQ ID NO: 31, a CDR2 as shown in SEQ ID NO: 32, and a CDR3 as shown in SEQ ID NO: 33 and
   a first $V_L$ comprising a CDR1 as shown in SEQ ID NO: 36, a CDR2 as shown in SEQ ID NO: 37, and a CDR3 as shown in SEQ ID NO: 38; or
   a second $V_L$ comprising a CDR1 as shown in SEQ ID NO: 41, a CDR2 as shown in SEQ ID NO: 42 and a CDR3 as shown in SEQ ID NO: 43.

2. The binding protein of claim 1, wherein the VH comprises an amino acid sequence shown in SEQ ID NO: 34.

3. The binding protein of claim 1, wherein the first $V_L$ comprises an amino acid sequence shown in SEQ ID NO: 39, and the second $V_L$ comprises an amino acid sequence shown in SEQ ID NO: 44.

4. An anti-LMA binding protein having an antigen binding domain that binds to LMA, the binding protein comprising:
   a $V_H$ comprising a CDR1 as shown in SEQ ID NO: 61, a CDR2 as shown in SEQ ID NO: 62, and a CDR3 as shown in SEQ ID NO: 63 and
   a first $V_L$ comprising a CDR1 as shown in SEQ ID NO: 66, a CDR2 as shown in SEQ ID NO: 67, and a CDR3 as shown in SEQ ID NO: 68; or
   a second $V_L$ comprising a CDR1 as shown in SEQ ID NO: 71, a CDR2 as shown in SEQ ID NO: 72, and a CDR3 as shown in SEQ ID NO: 73.

5. The binding protein of claim 4, wherein the $V_H$ comprises an amino acid sequence shown in SEQ ID NO: 64.

6. The binding protein of claim 4, wherein the first $V_L$ comprises an amino acid sequence shown in SEQ ID NO: 69, and the second $V_L$ comprises an amino acid sequence shown in SEQ ID NO: 74.

* * * * *

SEQUENCE LISTING

```
<160> NUMBER OF SEQ ID NOS: 94

<210> SEQ ID NO 1
<211> LENGTH: 5
<212> TYPE: PRT
<213> ORGANISM: Artificial Sequence
<220> FEATURE:
<223> OTHER INFORMATION: 7F11 heavy chain CDR1 amino acid sequence

<400> SEQUENCE: 1

Ser Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: 7F11 heavy chain CDR2 amino acid sequence

<400> SEQUENCE: 2

Ala Ile Asn Asn Ser Gly Gly Ser Thr Tyr Tyr Ala Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: 7F11 heavy chain CDR3 amino acid sequence

<400> SEQUENCE: 3

Asp Gln Gly Trp Gly Pro Leu Asn Trp Phe Asp Pro
```

```
1               5                    10
```

<210> SEQ ID NO 4
<211> LENGTH: 121
<212> TYPE: PRT
<213> ORGANISM: Artificial Sequence
<220> FEATURE:
<223> OTHER INFORMATION: 7F11 heavy chain frame work amino acid sequence

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Asn Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Gly Trp Gly Pro Leu Asn Trp Phe Asp Pro Trp Gly
            100                 105                 110

Gln Gly Thr Leu Val Thr Val Ser Ser
        115                 120
```

<210> SEQ ID NO 5
<211> LENGTH: 470
<212> TYPE: PRT
<213> ORGANISM: Artificial Sequence
<220> FEATURE:
<223> OTHER INFORMATION: 7F11 heavy chain full length amino acid
      sequence

<400> SEQUENCE: 5

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Asn Asn Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Gln Gly Trp Gly Pro Leu Asn Trp Phe Asp
        115                 120                 125

Pro Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175
```

```
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
            210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 6
<211> LENGTH: 11
<212> TYPE: PRT
<213> ORGANISM: Artificial Sequence
<220> FEATURE:
<223> OTHER INFORMATION: 7F11 light chain 1 CDR1 amino acid sequence

<400> SEQUENCE: 6

Arg Ala Ser Gln Gly Ile Ser Ser Trp Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: 7F11 light chain 1 CDR2 amino acid sequence
```

<400> SEQUENCE: 7

Ala Ala Ser Ser Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: 7F11 light chain 1 CDR3 amino acid sequence

<400> SEQUENCE: 8

Gln Gln Tyr Asn Ser His Pro Arg Thr
1               5

<210> SEQ ID NO 9
<211> LENGTH: 107
<212> TYPE: PRT
<213> ORGANISM: Artificial Sequence
<220> FEATURE:
<223> OTHER INFORMATION: 7F11 light chain 1 frame work amino acid
       sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Arg
                85                  90                  95

Thr Phe Gly Gln Gly Thr Lys Val Glu Ile Lys
            100                 105

<210> SEQ ID NO 10
<211> LENGTH: 236
<212> TYPE: PRT
<213> ORGANISM: Artificial Sequence
<220> FEATURE:
<223> OTHER INFORMATION: 7F11 light chain 1 full length amino acid
       sequence

<400> SEQUENCE: 10

Met Asp Met Arg Val Leu Ala Gln Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser His Pro Arg Thr Phe Gly Gln Gly Thr Lys Val Glu Ile
            115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 11
<211> LENGTH: 11
<212> TYPE: PRT
<213> ORGANISM: Artificial Sequence
<220> FEATURE:
<223> OTHER INFORMATION: 7F11 light chain 2 CDR1 amino acid sequence

<400> SEQUENCE: 11

Arg Ala Ser Gln Gly Ile Ser Ser Trp Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: 7F11 light chain 2 CDR2 amino acid sequence

<400> SEQUENCE: 12

Ala Ala Ser Ser Leu Gln Ser
1               5

<210> SEQ ID NO 13
<211> LENGTH: 7
<212> TYPE: PRT
<213> ORGANISM: Artificial Sequence
<220> FEATURE:
<223> OTHER INFORMATION: 7F11 light chain 2 CDR3 amino acid sequence

<400> SEQUENCE: 13

Gln Gln Tyr Asn Ser Tyr Pro
1               5

<210> SEQ ID NO 14
<211> LENGTH: 105
<212> TYPE: PRT
<213> ORGANISM: Artificial Sequence
<220> FEATURE:
<223> OTHER INFORMATION: 7F11 light chain 2 frame work amino acid
      sequence

<400> SEQUENCE: 14

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Gly Gly Gly Thr Lys Val Glu Ile Lys
            100                 105

<210> SEQ ID NO 15
<211> LENGTH: 234
<212> TYPE: PRT
<213> ORGANISM: Artificial Sequence
<220> FEATURE:
<223> OTHER INFORMATION: 7F11 light chain 2 full length amino acid
      sequence

<400> SEQUENCE: 15

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 16
<211> LENGTH: 30
<212> TYPE: DNA
```

```
<213> ORGANISM: Artificial Sequence
<220> FEATURE:
<223> OTHER INFORMATION: 7F11 heavy chain CDR1 DNA sequence

<400> SEQUENCE: 16
ggattcacct ttagcagcta tgccatgagc                                        30

<210> SEQ ID NO 17
<211> LENGTH: 51
<212> TYPE: DNA
<213> ORGANISM: Artificial Sequence
<220> FEATURE:
<223> OTHER INFORMATION: 7F11 heavy chain CDR2 DNA sequence

<400> SEQUENCE: 17
gctattaata atagtggtgg tagcacatac tacgcagact ccgtgaaggg c                51

<210> SEQ ID NO 18
<211> LENGTH: 36
<212> TYPE: DNA
<213> ORGANISM: Artificial Sequence
<220> FEATURE:
<223> OTHER INFORMATION: 7F11 heavy chain CDR3 DNA sequence

<400> SEQUENCE: 18
gatcagggct ggggacccct caactggttc gacccc                                 36

<210> SEQ ID NO 19
<211> LENGTH: 363
<212> TYPE: DNA
<213> ORGANISM: Artificial Sequence
<220> FEATURE:
<223> OTHER INFORMATION: 7F11 heavy chain frame work DNA sequence

<400> SEQUENCE: 19
gaggtgcagc tgttggagtc tgggggaggc ttggtacagc ctggggggtc cctgagactc        60
tcctgtgcag cctctggatt cacctttagc agctatgcca tgagctgggt ccgccaggct       120
ccagggaagg gctggagtg gtctcagct attaataata gtggtggtag cacatactac        180
gcagactccg tgaagggccg gttcaccatc tccagagaca attccaagaa cacgctgtat       240
ctgcaaatga acagcctgag agccgaggac acggccgtat attactgtgc gaaagatcag       300
ggctggggac ccctcaactg gttcgacccc tggggccagg gaaccctggt caccgtctcc       360
tca                                                                    363

<210> SEQ ID NO 20
<211> LENGTH: 1410
<212> TYPE: DNA
<213> ORGANISM: Artificial Sequence
<220> FEATURE:
<223> OTHER INFORMATION: 7F11 heavy chain full length DNA sequence

<400> SEQUENCE: 20
atggagtttg ggctgagctg ctttttctt gtggctattt taaaaggtgt ccagtgtgag        60
gtgcagctgt tggagtctgg gggaggcttg gtacagcctg ggggtccct gagactctcc       120 tgtgcagcct ctggattcac ctttagcagc tatgccatga gctgggtccg ccaggctcca      180 gggaagggc tggagtgggt ctcagctatt aataatagtg gtggtagcac atactacgca       240
gactccgtga agggccggtt caccatctcc agagacaatt ccaagaacac gctgtatctg      300
caaatgaaca gcctgagagc cgaggacacg gccgtatatt actgtgcgaa agatcagggc      360
tggggacccc tcaactggtt cgaccccctgg ggccagggaa ccctggtcac cgtctcctca    420
```

```
gcctccacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagag agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc catcgagaaa accatctcc    1080 aaagccaaag gcagccccg agaaccacag gtgtacaccc tgcccccatc ccgggatgag    1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa                                    1410

<210> SEQ ID NO 21
<211> LENGTH: 33
<212> TYPE: DNA
<213> ORGANISM: Artificial Sequence
<220> FEATURE:
<223> OTHER INFORMATION: 7F11 light chain 1 CDR1 DNA sequence

<400> SEQUENCE: 21
cgggcgagtc agggtattag cagctggtta gcc                                 33

<210> SEQ ID NO 22
<211> LENGTH: 21
<212> TYPE: DNA
<213> ORGANISM: Artificial Sequence
<220> FEATURE:
<223> OTHER INFORMATION: 7F11 light chain 1 CDR2 DNA sequence

<400> SEQUENCE: 22
gctgcatcca gtttgcaaag t                                              21

<210> SEQ ID NO 23
<211> LENGTH: 27
<212> TYPE: DNA
<213> ORGANISM: Artificial Sequence
<220> FEATURE:
<223> OTHER INFORMATION: 7F11 light chain 1 CDR3 DNA sequence

<400> SEQUENCE: 23
caacagtata atagtcaccc tcggacg                                        27

<210> SEQ ID NO 24
<211> LENGTH: 321
<212> TYPE: DNA
<213> ORGANISM: Artificial Sequence
<220> FEATURE:
<223> OTHER INFORMATION: 7F11 light chain 1 frame work DNA sequence
```

```
<400> SEQUENCE: 24
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtc accctcggac gttcggccaa   300
gggaccaagg tggaaatcaa a                                             321
```

<210> SEQ ID NO 25
<211> LENGTH: 708
<212> TYPE: DNA
<213> ORGANISM: Artificial Sequence
<220> FEATURE:
<223> OTHER INFORMATION: 7F11 light chain 1 full length DNA sequence

```
<400> SEQUENCE: 25
atggacatga gggtcctcgc tcagctcctg gggctcctgc tgctctgttt cccaggtgcc    60
agatgtgaca tccagatgac ccagtctcca tcctcactgt ctgcatctgt aggagacaga   120
gtcaccatca cttgtcgggc gagtcagggt attagcagct ggttagcctg gtatcagcag   180
aaaccagaga agcccctaa gtccctgatc tatgctgcat ccagtttgca aagtggggtc    240
ccatcaaggt tcagcggcag tggatctggg acagatttca ctctcaccat cagcagcctg   300
cagcctgaag attttgcaac ttattactgc caacagtata atagtcaccc tcggacgttc   360
ggccaaggga ccaaggtgga aatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt                708
```

<210> SEQ ID NO 26
<211> LENGTH: 33
<212> TYPE: DNA
<213> ORGANISM: Artificial Sequence
<220> FEATURE:
<223> OTHER INFORMATION: 7F11 light chain 2 CDR1 DNA sequence

```
<400> SEQUENCE: 26
cgggcgagtc agggtattag cagctggtta gcc                                 33
```

<210> SEQ ID NO 27
<211> LENGTH: 21
<212> TYPE: DNA
<213> ORGANISM: Artificial Sequence
<220> FEATURE:
<223> OTHER INFORMATION: 7F11 light chain 2 CDR2 DNA sequence

```
<400> SEQUENCE: 27
gctgcatcca gtttgcaaag t                                              21
```

<210> SEQ ID NO 28
<211> LENGTH: 21
<212> TYPE: DNA
<213> ORGANISM: Artificial Sequence
<220> FEATURE:
<223> OTHER INFORMATION: 7F11 light chain 2 CDR3 DNA sequence

<400> SEQUENCE: 28
caacagtata atagttaccc t                                           21

<210> SEQ ID NO 29
<211> LENGTH: 315
<212> TYPE: DNA
<213> ORGANISM: Artificial Sequence
<220> FEATURE:
<223> OTHER INFORMATION: 7F11 light chain 2 frame work DNA sequence

<400> SEQUENCE: 29
gacatccaga tgacccagtc tccatcctca ctgtctgcat ctgtaggaga cagagtcacc   60
atcacttgtc gggcgagtca gggtattagc agctggttag cctggtatca gcagaaacca  120
gagaaagccc ctaagtccct gatctatgct gcatccagtt tgcaaagtgg ggtcccatca  180
aggttcagcg gcagtggatc tgggacagat ttcactctca ccatcagcag cctgcagcct  240
gaagattttg caacttatta ctgccaacag tataatagtt accctttcgg cggagggacc  300
aaggtggaga tcaaa                                                  315

<210> SEQ ID NO 30
<211> LENGTH: 702
<212> TYPE: DNA
<213> ORGANISM: Artificial Sequence
<220> FEATURE:
<223> OTHER INFORMATION: 7F11 light chain 2 full length DNA sequence

<400> SEQUENCE: 30
atggacatga gggtcctcgc tcagctcctg gggctcctgc tgctctgttt cccaggtgcc   60
agatgtgaca tccagatgac ccagtctcca cctcactgt ctgcatctgt aggagacaga  120
gtcaccatca cttgtcgggc gagtcagggt attagcagct ggttagcctg gtatcagcag  180
aaaccagaga aagcccctaa gtccctgatc tatgctgcat ccagtttgca aagtggggtc  240
ccatcaaggt tcagcggcag tggatctggg acagatttca ctctcaccat cagcagcctg  300
cagcctgaag attttgcaac ttattactgc caacagtata atagttaccc tttcggcgga  360
gggaccaagg tggagatcaa acgaactgtg gctgcaccat ctgtcttcat cttcccgcca  420
tctgatgagc agttgaaatc tggaactgcc tctgttgtgt gcctgctgaa taacttctat  480
cccagagagg ccaaagtaca gtggaaggtg gataacgccc tccaatcggg taactcccag  540
gagagtgtca cagagcagga cagcaaggac agcacctaca gcctcagcag caccctgacg  600
ctgagcaaag cagactacga gaaacacaaa gtctacgcct gcgaagtcac ccatcagggc  660
ctgagctcgc ccgtcacaaa gagcttcaac aggggagagt gt                     702

<210> SEQ ID NO 31
<211> LENGTH: 5
<212> TYPE: PRT
<213> ORGANISM: Artificial Sequence
<220> FEATURE:
<223> OTHER INFORMATION: 18E8 heavy chain CDR1 amino acid sequence

<400> SEQUENCE: 31

Ser Tyr Ser Met Asn
1               5

<210> SEQ ID NO 32
<211> LENGTH: 17
<212> TYPE: PRT
<213> ORGANISM: Artificial Sequence

```
<220> FEATURE:
<223> OTHER INFORMATION: 18E8 heavy chain CDR2 amino acid sequence

<400> SEQUENCE: 32

Phe Ile Ser Ser Trp Ser Asn Tyr Ile Tyr Tyr Ala Asp Ser Val Lys
1               5                   10                  15

Gly

<210> SEQ ID NO 33
<211> LENGTH: 10
<212> TYPE: PRT
<213> ORGANISM: Artificial Sequence
<220> FEATURE:
<223> OTHER INFORMATION: 18E8 heavy chain CDR3 amino acid sequence

<400> SEQUENCE: 33

Leu Ala Asn Trp Gly Thr Tyr Phe Asp Cys
1               5                   10

<210> SEQ ID NO 34
<211> LENGTH: 119
<212> TYPE: PRT
<213> ORGANISM: Artificial Sequence
<220> FEATURE:
<223> OTHER INFORMATION: 18E8 heavy chain frame work amino acid sequence

<400> SEQUENCE: 34

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Phe Ile Ser Ser Trp Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Leu Ala Asn Trp Gly Thr Tyr Phe Asp Cys Trp Gly Gln Gly
            100                 105                 110

Thr Leu Val Thr Val Ser Ser
        115

<210> SEQ ID NO 35
<211> LENGTH: 468
<212> TYPE: PRT
<213> ORGANISM: Artificial Sequence
<220> FEATURE:
<223> OTHER INFORMATION: 18E8 heavy chain full length amino acid
      sequence

<400> SEQUENCE: 35

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60
```

```
Glu Trp Val Ser Phe Ile Ser Ser Trp Ser Asn Tyr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Ser Leu Ala Asn Trp Gly Thr Tyr Phe Asp Cys Trp
            115                 120                 125

Gly Gln Gly Thr Leu Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
    435                 440                 445

Met His Glu Ala Leu His Asn His Tyr Thr Gln Lys Ser Leu Ser Leu
450                 455                 460

Ser Pro Gly Lys
465
```

<210> SEQ ID NO 36
<211> LENGTH: 11
<212> TYPE: PRT
<213> ORGANISM: Artificial Sequence
<220> FEATURE:
<223> OTHER INFORMATION: 18E8 light chain 1 CDR1 amino acid sequence

<400> SEQUENCE: 36

```
Arg Ala Ser Gln Gly Ile Ser Ser Trp Leu Ala
1               5                   10
```

<210> SEQ ID NO 37
<211> LENGTH: 7
<212> TYPE: PRT
<213> ORGANISM: Artificial Sequence
<220> FEATURE:
<223> OTHER INFORMATION: 18E8 light chain 1 CDR2 amino acid sequence

<400> SEQUENCE: 37

```
Ala Ala Ser Ser Leu Gln Ser
1               5
```

<210> SEQ ID NO 38
<211> LENGTH: 9
<212> TYPE: PRT
<213> ORGANISM: Artificial Sequence
<220> FEATURE:
<223> OTHER INFORMATION: 18E8 light chain 1 CDR3 amino acid sequence

<400> SEQUENCE: 38

```
Gln Gln Tyr Asn Ser Tyr Pro Leu Thr
1               5
```

<210> SEQ ID NO 39
<211> LENGTH: 107
<212> TYPE: PRT
<213> ORGANISM: Artificial Sequence
<220> FEATURE:
<223> OTHER INFORMATION: 18E8 light chain 1 frame work amino acid
      sequence

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 40
<211> LENGTH: 236
<212> TYPE: PRT
<213> ORGANISM: Artificial Sequence
<220> FEATURE:
<223> OTHER INFORMATION: 18E8 light chain 1 full length amino acid
      sequence

<400> SEQUENCE: 40

```
Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 41
<211> LENGTH: 11
<212> TYPE: PRT
<213> ORGANISM: Artificial Sequence
<220> FEATURE:
<223> OTHER INFORMATION: 18E8 light chain 2 CDR1 amino acid sequence

<400> SEQUENCE: 41

```
Trp Ala Ser Gln Gly Ile Ser Ser Tyr Leu Ala
1               5                   10
```

<210> SEQ ID NO 42
<211> LENGTH: 7
<212> TYPE: PRT
<213> ORGANISM: Artificial Sequence
<220> FEATURE:
<223> OTHER INFORMATION: 18E8 light chain 2 CDR2 amino acid sequence

<400> SEQUENCE: 42

```
Phe Ala Ser Ser Leu Gln Ser
1               5
```

<210> SEQ ID NO 43
<211> LENGTH: 9
<212> TYPE: PRT
<213> ORGANISM: Artificial Sequence

```
<220> FEATURE:
<223> OTHER INFORMATION: 18E8 light chain 2 CDR3 amino acid sequence

<400> SEQUENCE: 43

Gln Gln Tyr Tyr Ser Thr Pro Leu Thr
1               5

<210> SEQ ID NO 44
<211> LENGTH: 107
<212> TYPE: PRT
<213> ORGANISM: Artificial Sequence
<220> FEATURE:
<223> OTHER INFORMATION: 18E8 light chain 2 frame work amino acid
      sequence

<400> SEQUENCE: 44

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Asn Pro Ala Lys Ala Pro Lys Leu Phe Ile
        35                  40                  45

Tyr Phe Ala Ser Ser Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Ser Cys Gln Gln Tyr Tyr Ser Thr Pro Leu
                85                  90                  95

Thr Phe Gly Gly Gly Thr Lys Val Glu Ile Lys
            100                 105

<210> SEQ ID NO 45
<211> LENGTH: 236
<212> TYPE: PRT
<213> ORGANISM: Artificial Sequence
<220> FEATURE:
<223> OTHER INFORMATION: 18E8 light chain 2 full length amino acid
      sequence

<400> SEQUENCE: 45

Met Asp Met Arg Val Pro Ala Gln Arg Leu Gly Leu Leu Leu Leu Trp
1               5                   10                  15

Phe Pro Gly Ala Arg Cys Ala Ile Arg Met Thr Gln Ser Pro Phe Ser
            20                  25                  30

Leu Ser Ala Ser Val Gly Asp Arg Val Thr Ile Thr Cys Trp Ala Ser
        35                  40                  45

Gln Gly Ile Ser Ser Tyr Leu Ala Trp Tyr Gln Gln Asn Pro Ala Lys
50                  55                  60

Ala Pro Lys Leu Phe Ile Tyr Phe Ala Ser Ser Leu Gln Ser Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Ser Cys Gln Gln
            100                 105                 110

Tyr Tyr Ser Thr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
```

```
145                 150                 155                 160
Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 46
<211> LENGTH: 15
<212> TYPE: DNA
<213> ORGANISM: Artificial Sequence
<220> FEATURE:
<223> OTHER INFORMATION: 18E8 heavy chain CDR1 DNA sequence

<400> SEQUENCE: 46
agctatagca tgaac                                                    15

<210> SEQ ID NO 47
<211> LENGTH: 51
<212> TYPE: DNA
<213> ORGANISM: Artificial Sequence
<220> FEATURE:
<223> OTHER INFORMATION: 18E8 heavy chain CDR2 DNA sequence

<400> SEQUENCE: 47
ttcattagta gttggagtaa ttacatatac tacgcagact cagtgaaggg c            51

<210> SEQ ID NO 48
<211> LENGTH: 30
<212> TYPE: DNA
<213> ORGANISM: Artificial Sequence
<220> FEATURE:
<223> OTHER INFORMATION: 18E8 heavy chain CDR3 DNA sequence

<400> SEQUENCE: 48
ctagctaact ggggaaccta ctttgactgc                                    30

<210> SEQ ID NO 49
<211> LENGTH: 357
<212> TYPE: DNA
<213> ORGANISM: Artificial Sequence
<220> FEATURE:
<223> OTHER INFORMATION: 18E8 heavy chain frame work DNA sequence

<400> SEQUENCE: 49
gaggtgcagc tggtggagtc tgggggaggc ctggtcaagc ctggggggtc cctgaaactc   60
tcctgtgcag cctctggatt caccttcagt agctatagca tgaactgggt ccgccaggct  120
ccagggaagg ggctggagtg ggtctcattc attagtagtt ggagtaatta catatactac  180
gcagactcag tgaagggccg attcaccatc tccagagaca acgccaagaa ctcactgtat  240
ctgcaaatga acagcctgag agccgaggac acggctgtgt attactgtgc gagcctagct  300
aactggggaa cctactttga ctgctggggc cagggaaccc tggtcaccgt ctcgtca     357

<210> SEQ ID NO 50
<211> LENGTH: 1404
<212> TYPE: DNA
```

<213> ORGANISM: Artificial Sequence
<220> FEATURE:
<223> OTHER INFORMATION: 18E8 heavy chain full length DNA sequence

<400> SEQUENCE: 50

```
atggaactgg ggctccgctg ggttttcctt gttgctattt tagaaggtgt ccagtgtgag    60
gtgcagctgg tggagtctgg gggaggcctg gtcaagcctg ggggtccct gaaactctcc   120
tgtgcagcct ctggattcac cttcagtagc tatagcatga actgggtccg ccaggctcca   180
gggaaggggc tggagtgggt ctcattcatt agtagttgga gtaattacat atactacgca   240
gactcagtga agggccgatt caccatctcc agagacaacg ccaagaactc actgtatctg   300
caaatgaaca gcctgagagc cgaggacacg gctgtgtatt actgtgcgag cctagctaac   360
tggggaacct acttttgactg ctggggccag ggaaccctgg tcaccgtctc gtcagcctcc   420
accaagggcc catcggtctt ccccctggca ccctcctcca gagcacctc tggggcaca    480
gcggccctgg gctgcctggt caaggactac ttccccgaac cggtgacggt gtcgtggaac   540
tcaggcgccc tgaccagcgg cgtgcacacc ttccggctg tcctacagtc ctcaggactc   600
tactccctca gcagcgtggt gaccgtgccc tccagcagct gggcaccca gacctacatc   660
tgcaacgtga atcacaagcc cagcaacacc aaggtggaca gagagttga gcccaaatct   720
tgtgacaaaa ctcacacatg cccaccgtgc ccagcacctg aactcctggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca agccgcggg aggagcagta caacagcacg   960
taccgtgtgg tcagcgtcct caccgtcctg caccaggact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga tgagctgacc  1140
aagaaccagg tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttcct ctacagcaag ctcaccgtgg acaagagcag gtggcagcag  1320
gggaacgtct tctcatgctc cgtgatgcat gaggctctgc acaaccacta cacgcagaag  1380
agcctctccc tgtctccggg taaa                                         1404
```

<210> SEQ ID NO 51
<211> LENGTH: 33
<212> TYPE: DNA
<213> ORGANISM: Artificial Sequence
<220> FEATURE:
<223> OTHER INFORMATION: 18E8 light chain 1 CDR1 DNA sequence

<400> SEQUENCE: 51

```
cgggcgagtc agggtattag cagctggtta gcc                                33
```

<210> SEQ ID NO 52
<211> LENGTH: 21
<212> TYPE: DNA
<213> ORGANISM: Artificial Sequence
<220> FEATURE:
<223> OTHER INFORMATION: 18E8 light chain 1 CDR2 DNA sequence

<400> SEQUENCE: 52

```
gctgcatcca gtttgcaaag t                                             21
```

<210> SEQ ID NO 53
<211> LENGTH: 27
<212> TYPE: DNA
<213> ORGANISM: Artificial Sequence
<220> FEATURE:
<223> OTHER INFORMATION: 18E8 light chain 1 CDR3 DNA sequence

<400> SEQUENCE: 53
caacagtata atagttaccc gctcact                                          27

<210> SEQ ID NO 54
<211> LENGTH: 321
<212> TYPE: DNA
<213> ORGANISM: Artificial Sequence
<220> FEATURE:
<223> OTHER INFORMATION: 18E8 light chain 1 frame work DNA sequence

<400> SEQUENCE: 54
gacatccaga tgacccagtc tccatcctca ctgtctgcat ctgtaggaga cagagtcacc      60
atcacttgtc gggcgagtca gggtattagc agctggttag cctggtatca gcagaaacca    120
gagaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtt acccgctcac tttcggcgga    300
gggaccaagg tggagatcaa a                                              321

<210> SEQ ID NO 55
<211> LENGTH: 708
<212> TYPE: DNA
<213> ORGANISM: Artificial Sequence
<220> FEATURE:
<223> OTHER INFORMATION: 18E8 light chain 1 full length DNA sequence

<400> SEQUENCE: 55
atggacatga gggtcctcgc tcagctcctg gggctcctgc tgctctgttt cccaggtgcc      60
agatgtgaca tccagatgac ccagtctcca tcctcactgt ctgcatctgt aggagacaga    120
gtcaccatca cttgtcgggc gagtcagggt attagcagct ggttagcctg gtatcagcag    180
aaaccagaga aagcccctaa gtccctgatc tatgctgcat ccagtttgca aagtggggtc    240
ccatcaaggt tcagcggcag tggatctggg acagatttca ctctcaccat cagcagcctg    300
cagcctgaag attttgcaac ttattactgc caacagtata atagttaccc gctcactttc    360
ggcggaggga ccaaggtgga gatcaaacga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                 708

<210> SEQ ID NO 56
<211> LENGTH: 33
<212> TYPE: DNA
<213> ORGANISM: Artificial Sequence
<220> FEATURE:
<223> OTHER INFORMATION: 18E8 light chain 2 CDR1 DNA sequence

<400> SEQUENCE: 56
tgggccagtc agggcattag cagttattta gcc                                  33

<210> SEQ ID NO 57
<211> LENGTH: 21
<212> TYPE: DNA
<213> ORGANISM: Artificial Sequence
<220> FEATURE:
<223> OTHER INFORMATION: 18E8 light chain 2 CDR2 DNA sequence

<400> SEQUENCE: 57

```
tttgcatcca gtttgcaaag t                                           21
```

<210> SEQ ID NO 58
<211> LENGTH: 27
<212> TYPE: DNA
<213> ORGANISM: Artificial Sequence
<220> FEATURE:
<223> OTHER INFORMATION: 18E8 light chain 2 CDR3 DNA sequence

<400> SEQUENCE: 58

```
caacagtatt atagtacccc gctcact                                     27
```

<210> SEQ ID NO 59
<211> LENGTH: 321
<212> TYPE: DNA
<213> ORGANISM: Artificial Sequence
<220> FEATURE:
<223> OTHER INFORMATION: 18E8 light chain 2 frame work DNA sequence

<400> SEQUENCE: 59

```
gccatccgga tgacccagtc tccattctcc ctgtctgcat ctgtaggaga cagagtcacc   60
atcacttgct gggccagtca gggcattagc agttatttag cctggtatca gcaaatccca  120
gcaaaagccc ctaagctctt catctatttt gcatccagtt tgcaaagtgg ggtcccatca  180
aggttcagcg gcagtggatc tgggacggat tacactctca ccatcagcag cctgcagcct  240
gaagattttg caacttattc ctgtcaacag tattatagta ccccgctcac tttcggcgga  300
gggaccaagg tggagatcaa a                                            321
```

<210> SEQ ID NO 60
<211> LENGTH: 708
<212> TYPE: DNA
<213> ORGANISM: Artificial Sequence
<220> FEATURE:
<223> OTHER INFORMATION: 18E8 light chain 2 full length DNA sequence

<400> SEQUENCE: 60

```
atggacatga gggtgcccgc tcagcgcctg gggctcctgc tgctctggtt cccaggtgcc   60
agatgtgcca tccggatgac ccagtctcca ttctccctgt ctgcatctgt aggagacaga  120
gtcaccatca cttgctgggc cagtcagggc attagcagtt atttagcctg gtatcagcaa  180
aatccagcaa aagcccctaa gctcttcatc tattttgcat ccagtttgca aagtggggtc  240
ccatcaaggt tcagcggcag tggatctggg acggattaca ctctcaccat cagcagcctg  300
cagcctgaag attttgcaac ttattcctgt caacagtatt atagtacccc gctcactttc  360
ggcggaggga ccaaggtgga gatcaaacga actgtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgt              708
```

<210> SEQ ID NO 61
<211> LENGTH: 5
<212> TYPE: PRT
<213> ORGANISM: Artificial Sequence
<220> FEATURE:
<223> OTHER INFORMATION: 10B3 heavy chain CDR1 amino acid sequence

<400> SEQUENCE: 61

Ser Tyr Ser Met Asn
1               5

<210> SEQ ID NO 62
<211> LENGTH: 17
<212> TYPE: PRT
<213> ORGANISM: Artificial Sequence
<220> FEATURE:
<223> OTHER INFORMATION: 10B3 heavy chain CDR2 amino acid sequence

<400> SEQUENCE: 62

Phe Ile Ser Ser Asn Arg Asn Tyr Ile Tyr Tyr Ala Asp Ser Val Lys
1               5                   10                  15

Gly

<210> SEQ ID NO 63
<211> LENGTH: 10
<212> TYPE: PRT
<213> ORGANISM: Artificial Sequence
<220> FEATURE:
<223> OTHER INFORMATION: 10B3 heavy chain CDR3 amino acid sequence

<400> SEQUENCE: 63

Leu Ala Asn Trp Gly Thr Tyr Phe Asp Tyr
1               5                   10

<210> SEQ ID NO 64
<211> LENGTH: 119
<212> TYPE: PRT
<213> ORGANISM: Artificial Sequence
<220> FEATURE:
<223> OTHER INFORMATION: 10B3 heavy chain frame work amino acid sequence

<400> SEQUENCE: 64

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Phe Ile Ser Ser Asn Arg Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Leu Ala Asn Trp Gly Thr Tyr Phe Asp Tyr Trp Gly Gln Gly
            100                 105                 110

Thr Leu Val Thr Val Ser Ser
        115

<210> SEQ ID NO 65
<211> LENGTH: 468

<212> TYPE: PRT
<213> ORGANISM: Artificial Sequence
<220> FEATURE:
<223> OTHER INFORMATION: 10B3 heavy chain full length amino acid sequence

<400> SEQUENCE: 65

```
Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Phe Ile Ser Ser Asn Arg Asn Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Leu Ala Asn Trp Gly Thr Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380
```

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
    435                 440                 445

Met His Glu Ala Leu His Asn His Tyr Thr Gln Lys Ser Leu Ser Leu
450                 455                 460

Ser Pro Gly Lys
465

<210> SEQ ID NO 66
<211> LENGTH: 11
<212> TYPE: PRT
<213> ORGANISM: Artificial Sequence
<220> FEATURE:
<223> OTHER INFORMATION: 10B3 light chain 1 CDR1 amino acid sequence

<400> SEQUENCE: 66

Arg Ala Ser Gln Gly Ile Ser Ser Trp Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: 10B3 light chain 1 CDR2 amino acid sequence

<400> SEQUENCE: 67

Ala Ala Ser Ser Leu Gln Ser
1               5

<210> SEQ ID NO 68
<211> LENGTH: 9
<212> TYPE: PRT
<213> ORGANISM: Artificial Sequence
<220> FEATURE:
<223> OTHER INFORMATION: 10B3 light chain 1 CDR3 amino acid sequence

<400> SEQUENCE: 68

Arg Gln Tyr Asn Ser Tyr Pro Leu Thr
1               5

<210> SEQ ID NO 69
<211> LENGTH: 107
<212> TYPE: PRT
<213> ORGANISM: Artificial Sequence
<220> FEATURE:
<223> OTHER INFORMATION: 10B3 light chain 1 frame work amino acid
      sequence

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly

```
                   50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Arg Gln Tyr Asn Ser Tyr Pro Leu
                 85                  90                  95

Thr Phe Gly Gly Gly Thr Lys Val Glu Ile Arg
            100                 105

<210> SEQ ID NO 70
<211> LENGTH: 236
<212> TYPE: PRT
<213> ORGANISM: Artificial Sequence
<220> FEATURE:
<223> OTHER INFORMATION: 10B3 light chain 1 full length amino acid
      sequence

<400> SEQUENCE: 70

Met Asp Met Arg Val Leu Ala Gln Leu Leu Gly Leu Leu Leu Leu Cys
 1               5                  10                  15

Phe Pro Gly Ala Arg Cys Asp Ile Gln Met Thr Gln Ser Pro Ser Ser
                 20                  25                  30

Leu Ser Ala Ser Val Gly Asp Arg Val Thr Ile Thr Cys Arg Ala Ser
             35                  40                  45

Gln Gly Ile Ser Ser Trp Leu Ala Trp Tyr Gln Gln Lys Pro Glu Lys
 50                  55                  60

Ala Pro Lys Ser Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Arg Gln
            100                 105                 110

Tyr Asn Ser Tyr Pro Leu Thr Phe Gly Gly Gly Thr Lys Val Glu Ile
            115                 120                 125

Arg Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 71
<211> LENGTH: 11
<212> TYPE: PRT
<213> ORGANISM: Artificial Sequence
<220> FEATURE:
<223> OTHER INFORMATION: 10B3 light chain 2 CDR1 amino acid sequence

<400> SEQUENCE: 71

Trp Ala Ser Gln Gly Ile Ser Ser Tyr Leu Ala
 1               5                  10
```

<210> SEQ ID NO 72
<211> LENGTH: 7
<212> TYPE: PRT
<213> ORGANISM: Artificial Sequence
<220> FEATURE:
<223> OTHER INFORMATION: 10B3 light chain 2 CDR2 amino acid sequence

<400> SEQUENCE: 72

Tyr Ala Ser Ser Leu Gln Ser
1               5

<210> SEQ ID NO 73
<211> LENGTH: 9
<212> TYPE: PRT
<213> ORGANISM: Artificial Sequence
<220> FEATURE:
<223> OTHER INFORMATION: 10B3 light chain 2 CDR3 amino acid sequence

<400> SEQUENCE: 73

Gln Gln Tyr Tyr Ser Thr Pro Leu Thr
1               5

<210> SEQ ID NO 74
<211> LENGTH: 107
<212> TYPE: PRT
<213> ORGANISM: Artificial Sequence
<220> FEATURE:
<223> OTHER INFORMATION: 10B3 light chain 2 frame work amino acid
      sequence

<400> SEQUENCE: 74

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Asn Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys
            100                 105

<210> SEQ ID NO 75
<211> LENGTH: 236
<212> TYPE: PRT
<213> ORGANISM: Artificial Sequence
<220> FEATURE:
<223> OTHER INFORMATION: 10B3 light chain 2 full length amino acid
      sequence

<400> SEQUENCE: 75

Met Asp Met Arg Val Pro Ala Gln Arg Leu Gly Leu Leu Leu Leu Trp
1               5                   10                  15

Phe Pro Gly Ala Arg Cys Ala Ile Arg Met Thr Gln Ser Pro Phe Ser
            20                  25                  30

Leu Ser Ala Ser Val Gly Asp Arg Val Thr Ile Thr Cys Trp Ala Ser
        35                  40                  45

| | | | | | | | | | | | | |
|---|---|---|---|---|---|---|---|---|---|---|---|---|
|Gln|Gly|Ile|Ser|Ser|Tyr|Leu|Ala|Trp|Tyr|Gln|Gln|Lys Pro Ala Lys|
| |50| | | |55| | | |60| | | |

Ala Pro Asn Leu Phe Ile Tyr Tyr Ala Ser Ser Leu Gln Ser Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

Tyr Tyr Ser Thr Pro Leu Thr Phe Gly Gly Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 76
<211> LENGTH: 15
<212> TYPE: DNA
<213> ORGANISM: Artificial Sequence
<220> FEATURE:
<223> OTHER INFORMATION: 10B3 heavy chain CDR1 DNA sequence

<400> SEQUENCE: 76
agctatagca tgaac                                                     15

<210> SEQ ID NO 77
<211> LENGTH: 51
<212> TYPE: DNA
<213> ORGANISM: Artificial Sequence
<220> FEATURE:
<223> OTHER INFORMATION: 10B3 heavy chain CDR2 DNA sequence

<400> SEQUENCE: 77
ttcattagta gtaatcgtaa ttacatatac tacgcagact cagtgaaggg c              51

<210> SEQ ID NO 78
<211> LENGTH: 30
<212> TYPE: DNA
<213> ORGANISM: Artificial Sequence
<220> FEATURE:
<223> OTHER INFORMATION: 10B3 heavy chain CDR3 DNA sequence

<400> SEQUENCE: 78
ctagctaact ggggaaccta ctttgactac                                     30

<210> SEQ ID NO 79
<211> LENGTH: 357
<212> TYPE: DNA
<213> ORGANISM: Artificial Sequence
<220> FEATURE:
<223> OTHER INFORMATION: 10B3 heavy chain frame work DNA sequence

<400> SEQUENCE: 79

```
gaggtgcagc tggtggagtc tgggggaggc ctggtcaagc ctggggggtc cctgagactc      60
tcctgtgcag cctctggatt caccttcagt agctatagca tgaactgggt ccgccaggct     120
ccagggaagg gctggagtg gtctcattc attagtagta atcgtaatta catatactac       180
gcagactcag tgaagggccg attcaccatc tccagagaca acgccaagaa ctcactgtat     240
ctgcaaatga acagcctgag agccgaggac acggctgtgt attactgtgc gagcctagct    300
aactggggaa cctactttga ctactggggc cagggaaccc tggtcaccgt ctcctca       357
```

<210> SEQ ID NO 80
<211> LENGTH: 1404
<212> TYPE: DNA
<213> ORGANISM: Artificial Sequence
<220> FEATURE:
<223> OTHER INFORMATION: 10B3 heavy chain full length DNA sequence

<400> SEQUENCE: 80

```
atggaactgg ggctccgctg ggttttcctt gttgctattt tagaaggtgt ccagtgtgag      60
gtgcagctgg tggagtctgg gggaggcctg gtcaagcctg gggggtccct gagactctcc    120
tgtgcagcct ctggattcac cttcagtagc tatagcatga actgggtccg ccaggctcca   180
gggaaggggc tggagtgggt ctcattcatt agtagtaatc gtaattacat atactacgca   240
gactcagtga agggccgatt caccatctcc agagacaacg ccaagaactc actgtatctg   300
caaatgaaca gcctgagagc cgaggacacg gctgtgtatt actgtgcgag cctagctaac   360
tggggaacct actttgacta ctggggccag ggaaccctgg tcaccgtctc ctcagcctcc   420
accaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660
tgcaacgtga atcacaagcc cagcaacacc aaggtggaca agagagttga gcccaaatct   720
tgtgacaaaa ctcacacatg cccaccgtgc ccagcacctg aactcctggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca aagccgcggg aggagcagta caacagcacg   960
taccgtgtgg tcagcgtcct caccgtcctg caccaggact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga tgagctgacc  1140
aagaaccagg tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttcct ctacagcaag ctcaccgtgg acaagagcag gtggcagcag  1320
gggaacgtct tctcatgctc cgtgatgcat gaggctctgc acaaccacta cacgcagaag  1380
agcctctccc tgtctccggg taaa                                          1404
```

<210> SEQ ID NO 81
<211> LENGTH: 33
<212> TYPE: DNA
<213> ORGANISM: Artificial Sequence
<220> FEATURE:

<223> OTHER INFORMATION: 10B3 light chain 1 CDR1 DNA sequence

<400> SEQUENCE: 81
cgggcgagtc agggtattag cagctggtta gcc                       33

<210> SEQ ID NO 82
<211> LENGTH: 21
<212> TYPE: DNA
<213> ORGANISM: Artificial Sequence
<220> FEATURE:
<223> OTHER INFORMATION: 10B3 light chain 1 CDR2 DNA sequence

<400> SEQUENCE: 82
gctgcatcca gtttgcaaag t                                    21

<210> SEQ ID NO 83
<211> LENGTH: 27
<212> TYPE: DNA
<213> ORGANISM: Artificial Sequence
<220> FEATURE:
<223> OTHER INFORMATION: 10B3 light chain 1 CDR3 DNA sequence

<400> SEQUENCE: 83
cgacagtata atagttaccc actcact                              27

<210> SEQ ID NO 84
<211> LENGTH: 321
<212> TYPE: DNA
<213> ORGANISM: Artificial Sequence
<220> FEATURE:
<223> OTHER INFORMATION: 10B3 light chain 1 frame work DNA sequence

<400> SEQUENCE: 84
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg gtcccatca   180 aggttcagcg gcagtggatc tgggacagat tcactctca ccatcagcag cctgcagcct   240
gaagattttg caacttatta ctgccgacag tataatagtt acccactcac tttcggcgga   300
gggaccaagg tggagatcag a                                            321

<210> SEQ ID NO 85
<211> LENGTH: 708
<212> TYPE: DNA
<213> ORGANISM: Artificial Sequence
<220> FEATURE:
<223> OTHER INFORMATION: 10B3 light chain 1 full length DNA sequence

<400> SEQUENCE: 85
atggacatga gggtcctcgc tcagctcctg gggctcctgc tgctctgttt cccaggtgcc    60
agatgtgaca tccagatgac ccagtctcca tcctcactgt ctgcatctgt aggagacaga   120
gtcaccatca cttgtcgggc gagtcagggt attagcagct ggttagcctg gtatcagcag   180
aaaccagaga agcccctaa gtccctgatc tatgctgcat ccagtttgca aagtggggtc   240
ccatcaaggt tcagcggcag tggatctggg acagatttca ctctcaccat cagcagcctg   300
cagcctgaag attttgcaac ttattactgc cgacagtata atagttaccc actcactttc   360
ggcggaggga ccaaggtgga gatcagacga actgtggctg caccatctgt cttcatcttc   420
ccgccatctg atgagcagtt gaaatctgga actgcctctt tgtgtgcct gctgaataac   480 ttctatccca gagaggccaa agtacagtgg aaggtggata cgccctcca atcgggtaac   540

```
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                 708
```

<210> SEQ ID NO 86
<211> LENGTH: 33
<212> TYPE: DNA
<213> ORGANISM: Artificial Sequence
<220> FEATURE:
<223> OTHER INFORMATION: 10B3 light chain 2 CDR1 DNA sequence

<400> SEQUENCE: 86

```
tgggccagtc agggcattag cagttattta gcc                                 33
```

<210> SEQ ID NO 87
<211> LENGTH: 21
<212> TYPE: DNA
<213> ORGANISM: Artificial Sequence
<220> FEATURE:
<223> OTHER INFORMATION: 10B3 light chain 2 CDR2 DNA sequence

<400> SEQUENCE: 87

```
tatgcatcca gtttgcaaag t                                              21
```

<210> SEQ ID NO 88
<211> LENGTH: 27
<212> TYPE: DNA
<213> ORGANISM: Artificial Sequence
<220> FEATURE:
<223> OTHER INFORMATION: 10B3 light chain 2 CDR3 DNA sequence

<400> SEQUENCE: 88

```
caacagtatt atagtacccc gctcact                                        27
```

<210> SEQ ID NO 89
<211> LENGTH: 321
<212> TYPE: DNA
<213> ORGANISM: Artificial Sequence
<220> FEATURE:
<223> OTHER INFORMATION: 10B3 light chain 2 frame work DNA sequence

<400> SEQUENCE: 89

```
gccatccgga tgacccagtc tccattctcc ctgtctgcat ctgtaggaga cagagtcacc    60
atcacttgct gggccagtca gggcattagc agttatttag cctggtatca gcaaaaacca    120
gcaaagcccc taacctctt catctattat gcatccagtt tgcaaagtgg ggtcccatca    180
aggttcagcg gcagtggatc tgggacggat acactctca ccatcagcag cctgcagcct    240
gaagattttg caacttatta ctgtcaacag tattatagta ccccgctcac tttcggcgga    300
gggaccaagg tggagatcaa a                                              321
```

<210> SEQ ID NO 90
<211> LENGTH: 708
<212> TYPE: DNA
<213> ORGANISM: Artificial Sequence
<220> FEATURE:
<223> OTHER INFORMATION: 10B3 light chain 2 full length DNA sequence

<400> SEQUENCE: 90

```
atggacatga gggtgcccgc tcagcgcctg gggctcctgc tgctctggtt cccaggtgcc    60
agatgtgcca tccggatgac ccagtctcca ttctccctgt ctgcatctgt aggagacaga    120
```

-continued

```
gtcaccatca cttgctgggc cagtcagggc attagcagtt atttagcctg gtatcagcaa    180
aaaccagcaa agcccctaa cctcttcatc tattatgcat ccagtttgca aagtggggtc    240
ccatcaaggt tcagcggcag tggatctggg acggattaca ctctcaccat cagcagcctg    300
cagcctgaag attttgcaac ttattactgt caacagtatt atagtacccc gctcactttc    360
ggcggaggga ccaaggtgga gatcaaacga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgcccteca atcgggtaac    540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                 708
```

<210> SEQ ID NO 91
<211> LENGTH: 8
<212> TYPE: PRT
<213> ORGANISM: Artificial Sequence
<220> FEATURE:
<223> OTHER INFORMATION: 4G7 epitope lambda isotype 2 and 3 epitope 1

<400> SEQUENCE: 91

Lys Ala Asp Gly Ser Pro Val Lys
1               5

<210> SEQ ID NO 92
<211> LENGTH: 8
<212> TYPE: PRT
<213> ORGANISM: Artificial Sequence
<220> FEATURE:
<223> OTHER INFORMATION: 4G7 epitope lambda isotype 2 and 3 epitope 2

<400> SEQUENCE: 92

Lys Ala Asp Ser Ser Pro Val Lys
1               5

<210> SEQ ID NO 93
<211> LENGTH: 4
<212> TYPE: PRT
<213> ORGANISM: Artificial Sequence
<220> FEATURE:
<223> OTHER INFORMATION: 4G7 epitope lambda isotype 1 epitope 1
<220> FEATURE:
<221> NAME/KEY: misc_feature
<222> LOCATION: (1)..(1)
<223> OTHER INFORMATION: Xaa can be any naturally occurring amino acid

<400> SEQUENCE: 93

Xaa Ser His Arg
1

<210> SEQ ID NO 94
<211> LENGTH: 4
<212> TYPE: PRT
<213> ORGANISM: Artificial Sequence
<220> FEATURE:
<223> OTHER INFORMATION: 4G7 epitope lambda isotype 1 epitope 2
<220> FEATURE:

```
<221> NAME/KEY: misc_feature
<222> LOCATION: (1)..(1)
<223> OTHER INFORMATION: Xaa can be any naturally occurring amino acid

<400> SEQUENCE: 94

Xaa Ser His Lys
1
```